US012800581B2

(12) United States Patent
Aburaya et al.

(10) Patent No.: US 12,800,581 B2
(45) Date of Patent: Nov. 17, 2026

(54) ASSAY APPARATUS

(71) Applicant: FUJIFILM Corporation, Tokyo (JP)

(72) Inventors: Yoshihiro Aburaya, Kanagawa (JP); Yasutake Tanaka, Kanagawa (JP); Daisuke Okamura, Kanagawa (JP); Hiroyasu Ishii, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 567 days.

(21) Appl. No.: 18/476,849

(22) Filed: Sep. 28, 2023

(65) Prior Publication Data

US 2024/0019427 A1 Jan. 18, 2024

Related U.S. Application Data

(63) Continuation of application No. PCT/JP2022/014197, filed on Mar. 25, 2022.

(30) Foreign Application Priority Data

Apr. 1, 2021 (JP) ................................ 2021-062943
Feb. 15, 2022 (JP) ................................ 2022-021601

(51) Int. Cl.
*B01L 3/00* (2006.01)
*B01D 15/08* (2006.01)
(Continued)

(52) U.S. Cl.
CPC ...... *G01N 33/54388* (2021.08); *B01L 3/5023* (2013.01); *B01L 2200/04* (2013.01);
(Continued)

(58) Field of Classification Search
CPC ....... G01N 33/54388; G01N 33/54387; G01N 21/8483; G01N 21/78; B01L 3/5023;
(Continued)

(56) References Cited

U.S. PATENT DOCUMENTS

2008/0019866 A1* 1/2008 Paek .................. B01L 3/50273
422/68.1
2013/0224768 A1* 8/2013 Arai ................ G01N 33/54366
436/501
2017/0307603 A1 10/2017 Wada

FOREIGN PATENT DOCUMENTS

EP 2 574 926 A1 4/2013
EP 3 246 704 A1 11/2017
(Continued)

OTHER PUBLICATIONS

Japanese Office Action for corresponding Japanese Application No. 2023-511150, dated Nov. 11, 2025, with English translation.
(Continued)

*Primary Examiner* — Oyeleye Alexander Alabi
(74) *Attorney, Agent, or Firm* — Birch, Stewart, Kolasch & Birch, LLP

(57) ABSTRACT

The assay apparatus includes a loading part into which a cartridge including a carrier and a case is attachably and detachably to be loaded, the carrier having an assay region in which a color development state changes depending on whether the sample is positive or negative, and an index region which is optically distinguishable from other regions regardless of whether a sample is positive or negative, the case accommodating the carrier; a light source that illuminates the observation region on the carrier including the assay region and the index region; an imaging unit that images the observation region; and a processor configured to acquire an image including the observation region from the imaging unit, detect a position of the index region from the acquired image, and specify a position of the assay region with reference to the detected position of the index region.

12 Claims, 18 Drawing Sheets

(51) Int. Cl.

| | |
|---|---|
| ***B01F 33/302*** | (2022.01) |
| ***B01F 33/3033*** | (2022.01) |
| ***B01J 8/00*** | (2006.01) |
| ***B01J 8/02*** | (2006.01) |
| ***B01J 20/285*** | (2006.01) |
| ***B01J 20/287*** | (2006.01) |
| ***B01J 20/32*** | (2006.01) |
| ***B01L 7/00*** | (2006.01) |
| ***B01L 9/00*** | (2006.01) |
| ***B65G 47/80*** | (2006.01) |
| ***B82Y 20/00*** | (2011.01) |
| ***B82Y 30/00*** | (2011.01) |
| ***B82Y 40/00*** | (2011.01) |
| ***C08L 5/08*** | (2006.01) |
| ***C12M 1/34*** | (2006.01) |
| ***C12M 3/06*** | (2006.01) |
| ***C12N 1/14*** | (2026.01) |
| ***C12N 1/20*** | (2026.01) |
| ***C12Q 1/02*** | (2006.01) |
| ***C12Q 1/6806*** | (2018.01) |
| ***C12Q 1/6844*** | (2018.01) |
| ***C12Q 1/6848*** | (2018.01) |
| ***C12Q 1/6851*** | (2018.01) |
| ***C12Q 1/686*** | (2018.01) |
| ***G01K 1/14*** | (2021.01) |
| ***G01N 1/44*** | (2006.01) |
| ***G01N 15/10*** | (2024.01) |
| ***G01N 15/14*** | (2024.01) |
| ***G01N 15/1433*** | (2024.01) |
| ***G01N 21/01*** | (2006.01) |
| ***G01N 21/03*** | (2006.01) |
| ***G01N 21/05*** | (2006.01) |
| ***G01N 21/29*** | (2006.01) |
| ***G01N 21/33*** | (2006.01) |
| ***G01N 21/35*** | (2014.01) |
| ***G01N 21/65*** | (2006.01) |
| ***G01N 21/75*** | (2006.01) |
| ***G01N 21/77*** | (2006.01) |
| ***G01N 27/07*** | (2006.01) |
| ***G01N 27/28*** | (2006.01) |
| ***G01N 27/416*** | (2006.01) |
| ***G01N 30/02*** | (2006.01) |
| ***G01N 30/60*** | (2006.01) |
| ***G01N 30/72*** | (2006.01) |
| ***G01N 31/10*** | (2006.01) |
| ***G01N 31/12*** | (2006.01) |
| ***G01N 33/543*** | (2006.01) |
| ***G01N 33/557*** | (2006.01) |
| ***G01N 33/564*** | (2006.01) |
| ***G01N 33/574*** | (2006.01) |
| ***G01N 33/575*** | (2026.01) |
| ***G01N 33/57515*** | (2026.01) |
| ***G01N 33/58*** | (2006.01) |
| ***G01N 33/68*** | (2006.01) |
| ***G01N 33/72*** | (2006.01) |
| ***G01N 35/00*** | (2006.01) |
| ***H05B 45/10*** | (2020.01) |

(52) U.S. Cl.

CPC ... *B01L 2200/16* (2013.01); *B01L 2300/0654* (2013.01); *B01L 2300/069* (2013.01); *B01L 2300/0825* (2013.01)

(58) Field of Classification Search

CPC ............. B01L 2200/04; B01L 2200/16; B01L 2300/0654; B01L 2300/069; B01L 2300/0825

See application file for complete search history.

(56) References Cited

FOREIGN PATENT DOCUMENTS

| | | | | | |
|---|---|---|---|---|---|
| EP | 3 859 337 | A1 | | 8/2021 | |
| JP | 2005-331507 | A | | 12/2005 | |
| JP | 2008-523386 | A | | 7/2008 | |
| JP | 2010-101758 | A | | 5/2010 | |
| JP | 2012-198083 | A | | 10/2012 | |
| WO | WO 2012/042815 | A1 | | 4/2012 | |
| WO | WO-2014077142 | A1 | * | 5/2014 | ....... G01N 33/54388 |
| WO | WO 2016/114122 | A1 | | 7/2016 | |
| WO | WO 2018/191156 | A1 | | 10/2018 | |
| WO | WO 2020/066977 | A1 | | 4/2020 | |
| WO | WO 2021/004564 | A2 | | 1/2021 | |

OTHER PUBLICATIONS

Extended European Search Report for European Application No. 22780526.4, dated Nov. 8, 2024.

International Preliminary Report on Patentability and English translation of the Written Opinion of the International Searching Authority for International Application No. PCT/JP2022/014197, dated Oct. 12, 2023.

International Search Report for International Application No. PCT/JP2022/014197, dated Jun. 7, 2022, with English translation.

* cited by examiner

ASSAY APPARATUS

CROSS-REFERENCE TO RELATED APPLICATIONS

This application is a continuation of International Application No. PCT/JP2022/014197, filed on Mar. 25, 2022, which claims priority from Japanese Patent Application No. 2021-062943, filed on Apr. 1, 2021 and Japanese Patent Application No. 2022-021601, filed on Feb. 15, 2022. The entire disclosure of each of the above applications is incorporated herein by reference.

BACKGROUND

1. Technical Field

The technology of the present disclosure relates to an assay apparatus used for an immunochromatographic assay.

2. Related Art

JP2005-331507A describes a test piece measuring device to which a chromatographic carrier (hereinafter, referred to as a carrier) is attached and to which a test piece is to be attached. In this test piece measuring device, the test piece is positioned in the test piece measuring device, and the coloration region on the carrier to which the specimen is added is irradiated with the irradiation light from the light source. Such a coloration region is referred to as an assay region or the like. Then, the light receiving section detects the light reflected by or transmitted in the coloration region, and the operation device determines whether the specimen is positive or negative based on the detection result. In a case where the relative positions of the light source and the light receiving section, and the coloration region are not accurately positioned, the state of the coloration region may not be accurately detected, and the assay accuracy may decrease. In the test piece measuring device, in order to position the light source and the light receiving section, and the coloration region, such as by accurately irradiating the coloration region with the irradiation light from the light source, the test piece in the device is biased to the target position by using an elastic body such as a spring.

SUMMARY

The test piece described in JP2005-331507A may be referred to as a cartridge or the like, and the test piece measuring device may be referred to as an assay apparatus. The cartridge comprises a case that accommodates the carrier. In such a cartridge, the position of the carrier may be displaced with respect to the case because of individual differences in the cartridges. In such a case, even in a case where the case is biased to the target position as described in JP2005-331507A, the relative positions of the assay region on the carrier with respect to the light source and the light receiving section cannot be positioned. The misregistration of the carrier in the case occurs because of an error during manufacturing of the cartridge, or the like.

Since the color development state of the assay region does not change in a case where the sample is negative, the assay region cannot be optically distinguished from other regions of the carrier, which are the background of the assay region. In addition, even in a case where the sample is positive, the change in the color development state of the assay region may be very weak. In this case, in a state where the position of the assay region is not specified, it is difficult to optically distinguish the change in the color development state from the noise present in the other region, and erroneous recognition is likely to occur. Therefore, in a case where the misregistration of the relative positions of the assay region with respect to the light source and the light receiving section occurs because of individual differences of the cartridges, a region other than the assay region may be erroneously recognized as an assay region, resulting in erroneous determination.

In order to suppress such erroneous determination, a method of reliably specifying the position of the assay region regardless of the presence or absence of the misregistration due to the individual difference of the cartridge, is required.

In view of the above facts, the technique according to the present disclosure provides an assay apparatus capable of specifying the position of the assay region on the carrier even in a case where a misregistration due to an individual difference of the cartridge is present.

The assay apparatus of the present disclosure is an assay apparatus used for immunochromatographic assay, the assay apparatus including a loading part into which a cartridge including a carrier and a case for accommodating the carrier is attachably and detachably to be loaded, the carrier having an assay region in which a color development state changes depending on whether a sample is positive or negative, and an index region which is disposed with a preset interval from the assay region and which is optically distinguishable from other regions regardless of whether the sample is positive or negative; a light source that illuminates an observation region on the carrier including the assay region and the index region; an imaging unit that images the observation region; and a processor configured to acquire an image including the observation region from the imaging unit, detect a position of the index region from the acquired image, and specify a position of the assay region with reference to the detected position of the index region.

In the assay apparatus of the present disclosure, the index region is preferably a region in which a color development state changes by reacting with a reagent.

In the assay apparatus of the present disclosure, the processor is preferably configured to detect the position of the index region based on an optical density of the index region.

In the assay apparatus of the present disclosure, as the optical density, in the carrier, a ΔOD value, which is a difference between an optical density in the index region and an optical density in a background region serving as a background of the index region, is preferably used.

In the assay apparatus of the present disclosure, the processor is preferably configured to detect the position of the index region based on a form of the index region.

In the assay apparatus of the present disclosure, it is preferable that the light source is a white color light source, the image is a color image, and the processor is configured to detect the position of the index region based on a color of the index region.

In the assay apparatus of the present disclosure, preferably, in a case where the index region is a first color before reacting with a reagent and changes from the first color to a second color by reacting with the reagent, the light source includes a first monochromatic light source that emits first monochromatic light in which an amount of reflected light is larger in a case where the index region of the first color is irradiated as compared with a case where the index region of the second color is irradiated, and a second monochromatic light source that emits second monochromatic light in which an amount of reflected light is larger in a case where the index region of the second color is irradiated as compared with in a case where the index region of the first color is irradiated, and the processor is configured to acquire a first image obtained by imaging the index region of the second color using the first monochromatic light source and the imaging unit, acquire a second image obtained by imaging the index region of the second color using the second monochromatic light source and the imaging unit, and detect the position of the index region based on the first image and the second image.

In the assay apparatus of the present disclosure, it is preferable that the first color includes a green color component, the second color is orange color, the first monochromatic light source is a green color light source, and the second monochromatic light source is a red color light source.

In the assay apparatus of the present disclosure, it is preferable that a reagent is an amplifying liquid for amplifying the change in the color development state of the assay region, and the color development state of the index region changes by reacting with the amplifying liquid.

In the assay apparatus of the present disclosure, the index region is preferably a region in which a color development state changes by reacting with a labeling substance.

In the assay apparatus of the present disclosure, it is preferable that in the cartridge, the assay region and the index region are regions formed by coating on the carrier, and the carrier is assembled to the case after the assay region and the index region are formed.

In the assay apparatus of the present disclosure, preferably, an observation window for observing the observation region from an outside is formed in the cartridge, both of an outer shape of the cartridge and the observation window have a rectangular shape, the assay apparatus further includes a biasing unit for pressing an edge surface of the cartridge attached to the loading part against a reference surface, and the processor is configured to acquire, from the imaging unit, an image obtained by imaging a region at least including the entire observation window and a part of an outline of the cartridge in a state where the cartridge is pressed against the reference surface, and execute a trimming processing in which the observation region is cut out from the acquired image, and which includes a region-specifying processing in which the observation region is specified, in the image, by searching the outline and by searching at least a part of the observation window with reference to the searched outline.

In the assay apparatus of the present disclosure, the region-specifying processing in the trimming processing may be a processing in which the observation region is specified by searching the at least a part of the observation window of the cartridge in the image to specify a frame line of the observation window, and further by searching a boundary between the frame line and the carrier or a boundary between the blank in a region within the frame line and the carrier.

According to the assay apparatus of the present disclosure, the position of the assay region on the carrier can be specified even in a case where a misalignment due to an individual difference of the cartridge is present.

DESCRIPTION OF EMBODIMENTS

Figure 1:
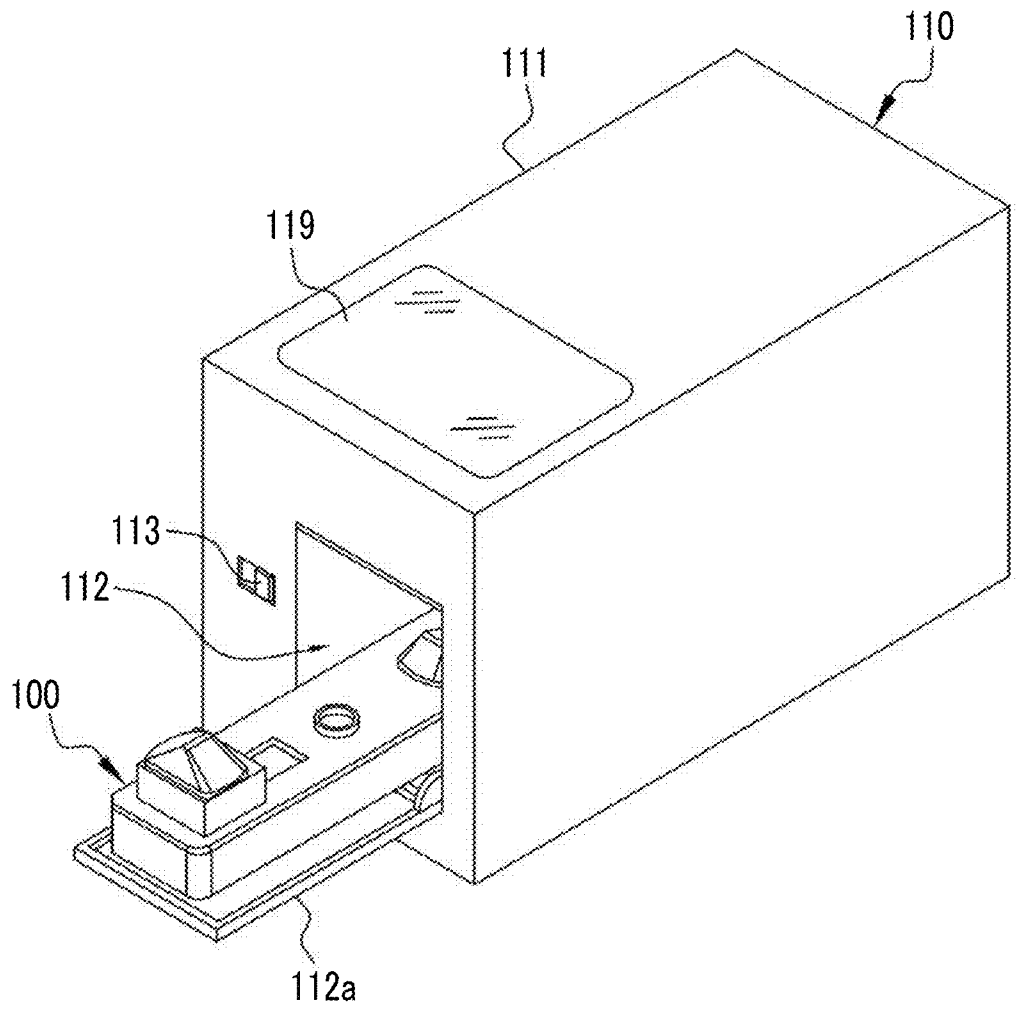
FIG. 1 is a perspective view showing an appearance of an assay apparatus according to the present disclosure.

Hereinafter, an assay apparatus according to an embodiment of the present invention is described with reference to the drawings. The constituent elements indicated by the same reference numerals in the drawings mean the same constituent elements. However, unless otherwise specified in the specification, each constituent element is not limited to one, and a plurality of each constituent element may be present.

The directions indicated by the arrows X and Y, which are appropriately shown in the respective figures, are directions along the horizontal plane and are orthogonal to each other. In addition, the direction indicated by the arrow Z is a direction along the perpendicular direction (vertical direction). The directions indicated by the arrows X, Y, and Z in respective figures coincide with each other.

<Overview of Immunochromatographic Assay Apparatus and Assay Cartridge>

Figure 2:
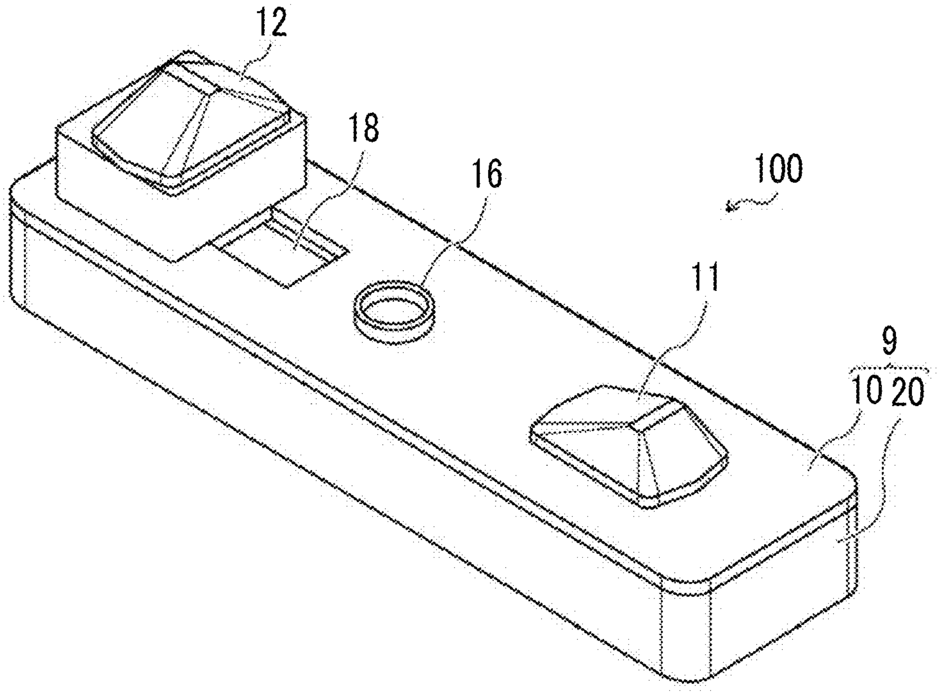
FIG. 2 is a perspective view of an assay cartridge to be loaded into the assay apparatus according to the present disclosure.
Figure 3:
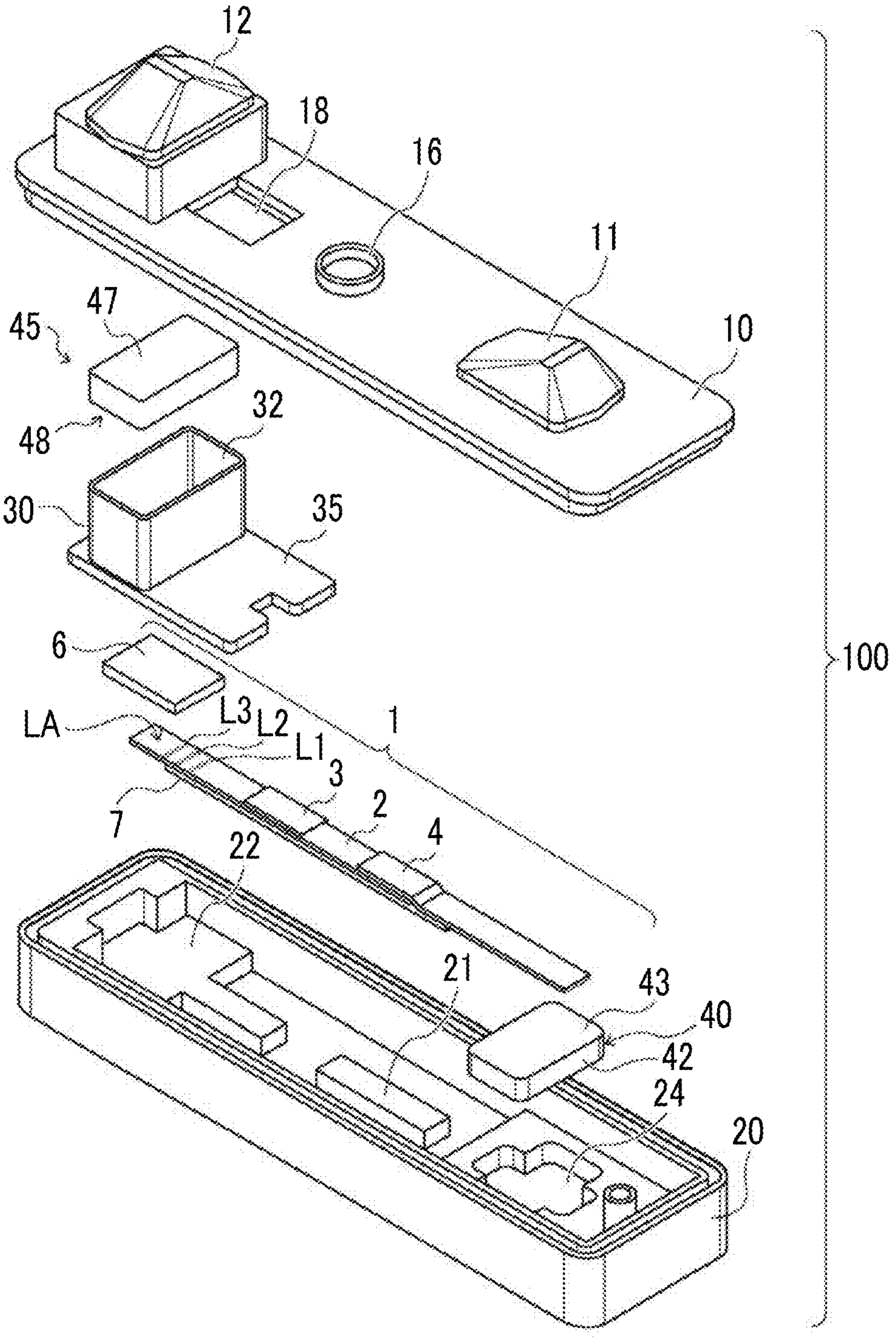
FIG. 3 is an exploded perspective view of the assay cartridge according to the present disclosure.

FIG. 1 is a perspective view showing the appearance of an immunochromatographic assay apparatus 110 (hereinafter, simply referred to as an assay apparatus 110) according to one embodiment. FIG. 2 is an external view of a cartridge 100 which is an assay cartridge to be attached into the assay apparatus 110, and FIG. 3 is an exploded perspective view of the cartridge 100. FIG. 4 is a diagram showing a state where a first pressing operation part 11 and a second pressing operation part 12 provided in the cartridge 100 are operated. FIG. 5 is a diagram showing the main accommodated components in the cartridge 100.

The cartridge 100 is a single-use type that is used one by one in each sample of assay target. As shown in FIG. 3, an assay strip 1 including an immunochromatographic carrier 2 (hereinafter, referred to as a carrier 2) is provided in the cartridge 100. An assay region L1 is provided in the carrier 2, and the color development state changes depending on whether or not the sample contains a test substance, that is, whether the sample is positive or negative.

The "change in color development state" includes any of an aspect in which a first color different from the color of the carrier 2 changes to another second color (that is, a color change), an aspect in which the color of the carrier 2 changes to another color by developing a color different from that of the carrier 2 (that is, color development), and an aspect in which the density of the color changes (that is, a change in density).

The sample is simply required to be a specimen that may contain a test substance, and the sample is not particularly limited. The sample is, for example, a biological specimen, particularly body fluid or excrement of an animal (particularly, a human) such as blood, serum, blood plasma, spinal fluid, tear fluid, sweat, urine, pus, nasal mucus, nasal swab, throat swab, nasal aspirate, or sputum, an organ, a tissue, a mucous membrane and skin, or swabs containing them, or a liquid specimen containing animals and plants themselves or a dried body thereof. Examples of the test substance include an antigen, an antibody, a protein, and a low-molecular-weight compound.

In the assay apparatus 110 of the present example, the cartridge 100 in a state where the sample is spotted is loaded. Then, the assay apparatus 110 detects a color development state of the assay region L1 of the loaded cartridge 100, and presents the determination result of whether the sample is positive or negative. In a case where a plurality of samples are assayed, the cartridge 100 for each sample is loaded one by one into the assay apparatus 110.

Hereinafter, the cartridge 100 is described on the premise that the cartridge 100 is loaded into the assay apparatus 110. However, the cartridge 100 of the present example has a configuration that a user can confirm visually whether the sample is positive or negative without using the assay apparatus 110. Such a cartridge 100 is also referred to as an immunochromatographic assay tool, an immunochromatographic assay kit, or the like.

<Assay Cartridge>

As shown in FIG. 2 and FIG. 3, as an example, the cartridge 100 includes a case 9 constituted of a case main body 20 and a cover member 10. The case 9 is formed of, for example, a resin material. An opening is formed in an upper part of the case main body 20, and in addition to the assay strip 1, a first reagent holding part 40, a second reagent holding part 45, and the like are accommodated therein. The cover member 10 covers the opening of the case main body 20 by being attached to the opening part of the case main body 20. The case 9 has an elongated shape as a whole in accordance with the elongated shape of the assay strip 1.

In the present example, a dropping port 16, an observation window 18, a first pressing operation part 11, and a second pressing operation part 12 are provided on an upper part of the case 9 constituted of the cover member 10. Each of these parts is integrally molded with the cover member 10 as an example. The dropping port 16 is an opening for adding dropwise a sample into the inside of the case 9. On the edge of the dropping port 16, a boss is vertically provided toward the upper part.

(Observation Window)

The observation window 18 is an opening portion for observing the assay region L1 from the outside, and is an opening portion that is illuminated by a light source 115 (see FIG. 8) which is described later, in the assay apparatus 110. In the present example, the size of the observation window 18 is a size such that, in addition to the assay region L1, the control region L2 and the color development region L3, which are described later, can also be observed. In the present specification, a region that is used for the determination of the assay region L1 of a region that includes the assay region L1, the control region L2, the color development region L3, and the peripheral region thereof and that can be observed from the observation window 18 is referred to as an observation region LA. The detection unit 114 (see FIG. 8), which is described later, images the observation region LA through the observation window 18. Then, the processor 120 specifies the position of the assay region L1 in the observation region LA based on the captured image imaged by the detection unit 114, and determines whether the sample is positive or negative by discriminating the change in the color development state. The observation region LA may be a region that can be observed from the observation window 18, that is, an entire region exposed to the observation window 18 (hereinafter, referred to as an exposed region EA), or may be a specific region within the exposed region EA. Details of the observation region LA are described later.

(First Pressing Operation Part, Second Pressing Operation Part)

As shown in FIG. 2, FIG. 3, and FIG. 4, the first pressing operation part 11 is an operating part operated to supply a first reagent 41 in the first reagent holding part 40 to the carrier 2. The second pressing operation part 12 is an operating part operated to supply a second reagent 46 in the second reagent holding part 45 to the carrier 2. As described later, the first reagent 41 and the second reagent 46 are amplifying liquids for amplifying the color development in the assay region L1 in a case where the sample is positive.

Figure 4A:
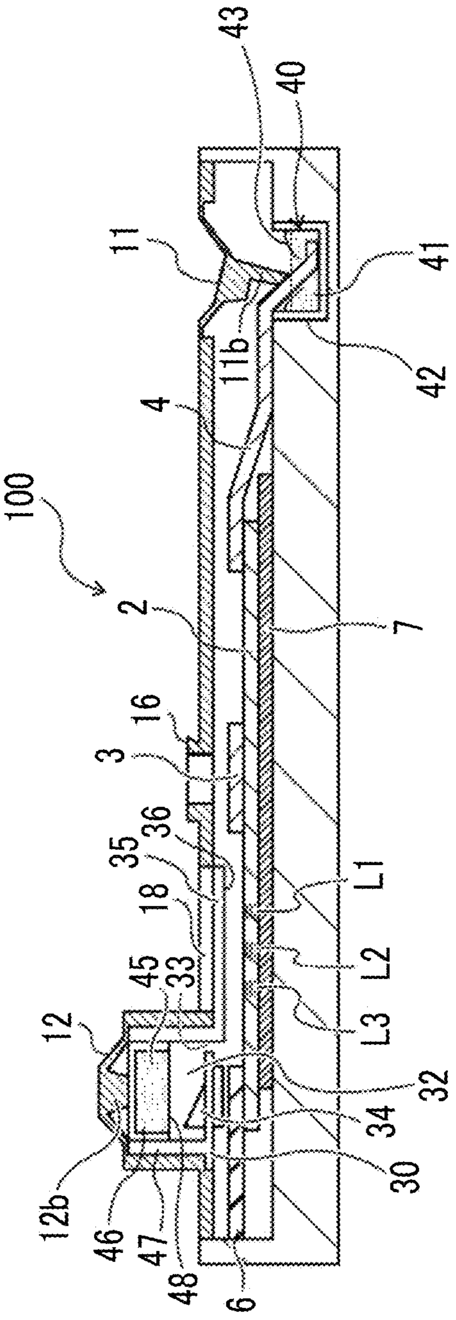
FIG. 4A is a cross-sectional view showing a state where a first pressing operation part is operated in the assay cartridge according to the present disclosure.
Figure 5:
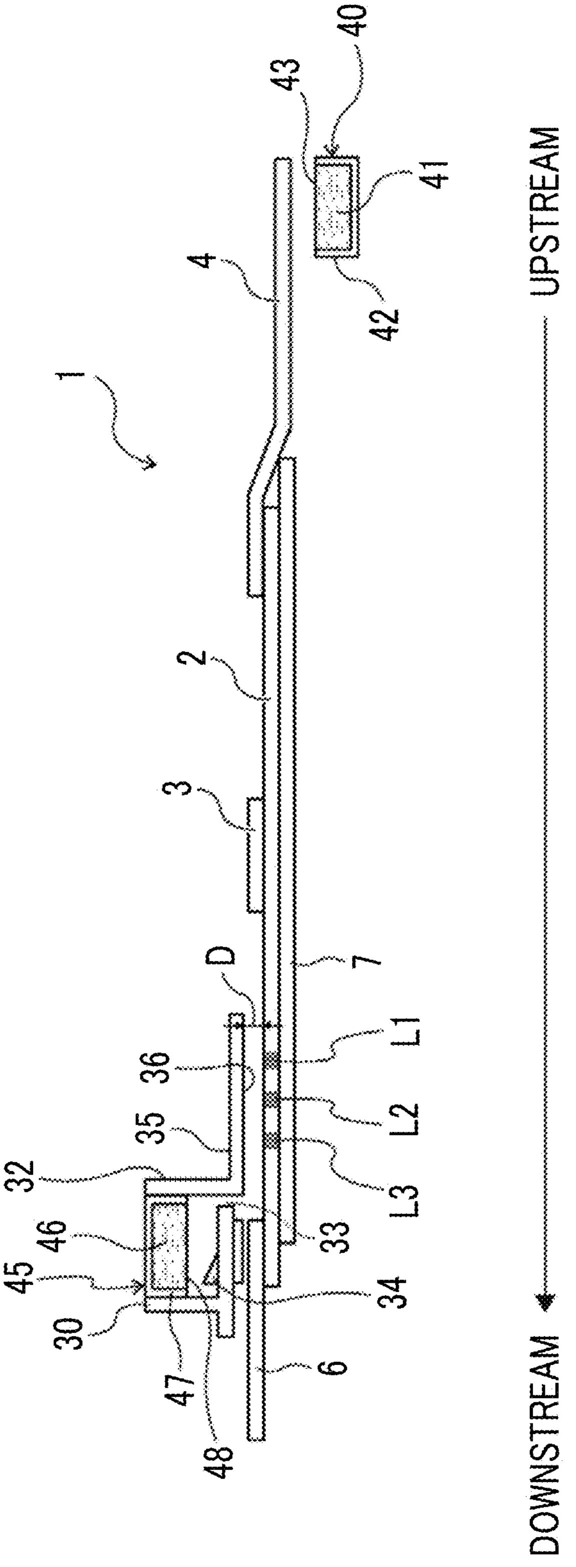
FIG. 5 is a side view showing a positional relationship between an assay strip, a multifunctional member, a first reagent holding part, and a second reagent holding part, in the assay cartridge according to the present disclosure.

As shown in FIG. 4A, in a case where a pressing force is applied from the outside as an external force to the first pressing operation part 11 by a pressing operation by a user, or the like, the first pressing operation part 11 is deformed. As shown in FIG. 2, as an example, the first pressing operation part 11 has a quadrangular pyramid shape, and in a case where a pressing force is applied from above to a region including the apex of the quadrangular pyramid, as shown in FIG. 4A, the first pressing operation part 11 is deformed such that the apex of the quadrangular pyramid sinks into the inside of the case 9. In a case of where the first pressing operation part 11 is deformed in this manner, a pressing force is applied to the first reagent holding part 40 inside the case 9. In the first reagent holding part 40, deformation or the like occurs because of a pressing force applied through the first pressing operation part 11. Because of this deformation or the like, the first reagent 41 held by the first reagent holding part 40 is supplied to the assay strip 1.

In addition, the first pressing operation part 11 is deformed by pressing and then the deformed state is maintained. Accordingly, after the first pressing operation part 11 is pressed, the supply of the first reagent 41 to the assay strip 1 is continued.

Figure 4B:
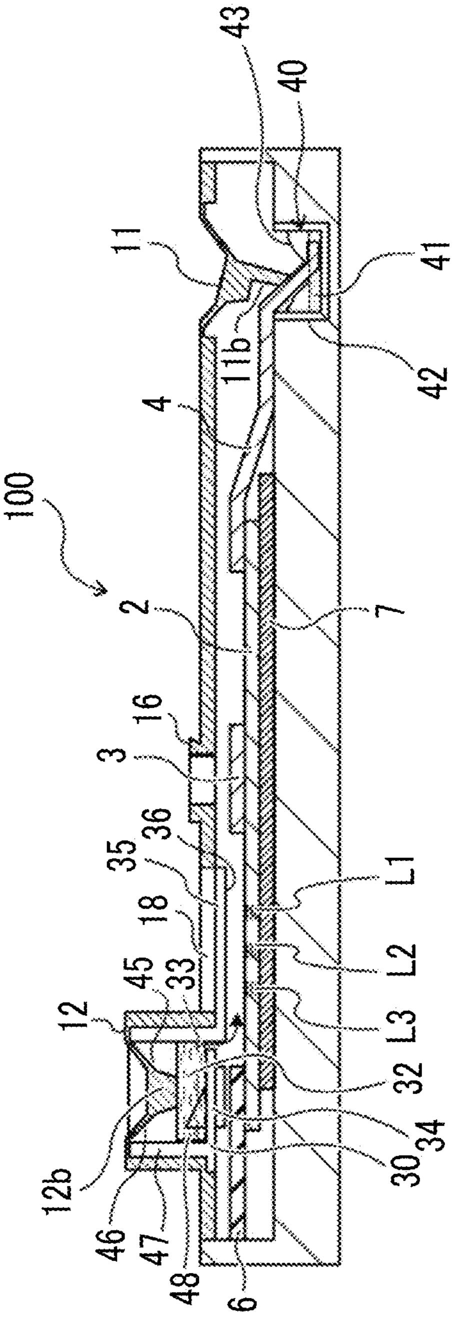
FIG. 4B is a cross-sectional view showing a state where the first pressing operation part and a second pressing operation part are operated.

Similarly, as shown in FIG. 4B, in a case where a pressing force is applied from the outside as an external force to the second pressing operation part 12, the second pressing operation part 12 is deformed. As shown in FIG. 2, similarly to the first pressing operation part 11, the second pressing operation part 12 of the present example also has a quadrangular pyramid shape, and in a case where a pressing force is applied from above to a region including the apex of the quadrangular pyramid, as shown in FIG. 4B, the second pressing operation part 12 is deformed such that the apex of the quadrangular pyramid sinks into the inside of the case 9. In a case of where the second pressing operation part 12 is deformed in this manner, a pressing force is applied to the second reagent holding part 45 inside the case 9. In the second reagent holding part 45, deformation or the like occurs because of a pressing force applied through the second pressing operation part 12. Because of this deformation or the like, the second reagent 46 held by the second reagent holding part 45 is supplied to the assay strip 1. In the second pressing operation part 12 of the present example, an abutting part 12*b* that abuts on the second reagent holding part 45 is provided in the inside of the case 9.

(First Reagent Holding Part)

As shown in FIG. 3, the case main body 20 accommodates the assay strip 1 including the carrier 2 along the longitudinal direction. As shown in FIG. 3 and FIG. 4, in the case main body 20, the first reagent holding part 40 is disposed on one end part side (upstream side shown in FIG. 5) in the longitudinal direction. In the case main body 20, in a portion where the first reagent holding part 40 is disposed, the first accommodating part 24 having a recess-shaped in accordance with the shape of the first reagent holding part 40 is formed. One end part of the assay strip 1 is disposed above the first reagent holding part 40 in a state of being accommodated in the first accommodating part 24.

As shown in FIG. 4 and FIG. 5, the first reagent holding part 40 holds the first reagent 41. The first reagent holding part 40 is constituted of, for example, a container 42 formed of a resin material and having an opening on one surface, and a sheet member 43 that covers the opening of the container 42 and that is breakable. The container 42 is filled with the first reagent 41, and the opening of the container 42 is sealed by the sheet member 43. The first reagent holding part 40 is disposed in the first accommodating part 24 in a posture in which the sheet member 43 faces upward.

The pressing force applied from the first pressing operation part 11 is transmitted to the sheet member 43 of the first reagent holding part 40 via the end part of the assay strip 1 to break the sheet member 43. The sheet member 43 is broken, and thus the first reagent 41 is supplied to the assay strip 1. In the first pressing operation part 11 of the present example, a protruding part 11*b* that abuts on the sheet member 43. The protruding part 11*b* has, for example, an elongated shape extending in the longitudinal direction in the width direction of the assay strip 1 and has a tip with a pointed shape toward the sheet member 43, such that the sheet member 43 is easily broken.

(Multifunctional Member)

In addition, the cartridge 100 includes a multifunctional member 30 having a function of accommodating the second reagent holding part 45. The multifunctional member 30 is disposed on the other end part side (downstream side shown in FIG. 5) of the case main body 20 and above the assay strip 1. The multifunctional member 30 is a member in which the second accommodating part 32 and the flow channel forming part 35 are integrally formed. The second accommodating part 32 is a part accommodating the second reagent holding part 45. The second accommodating part 32 has a box shape having an opened upper surface. As shown in FIG. 4 and FIG. 5, on the bottom of the second accommodating part 32, a protrusion 34 for breaking a sheet member 48, which is described later, of the second reagent holding part 45, and an opening 33 that allows to flow the second reagent 46 flowed out from the second reagent holding part 45, toward the assay strip 1.

Furthermore, the flow channel forming part 35 is provided to be connected to the upstream side from the second accommodating part 32. The flow channel forming part 35 has a flat plate shape, is disposed at a position facing the assay region L1 or the like in the longitudinal direction of the assay strip 1, and is disposed with an interval from the assay strip 1. Then, between the flow channel forming part 35 and the assay strip 1, a flow channel for flowing the second reagent 46 flowed out from the second accommodating part 32 toward the assay region L1 or the like is formed. In addition, the flow channel forming part 35 is disposed between the observation window 18 and the assay region L1 or the like of the assay strip 1. Therefore, the flow channel forming part 35 is formed of a transparent member and thus the assay region L1 and the like can be observed through the observation window 18.

(Second Reagent Holding Part)

The second reagent holding part 45 holds the second reagent 46. The second reagent holding part 45 is constituted of, for example, a container 47 formed of a resin material and having an opening on one surface, and a sheet member 48 that covers the opening of the container 47 and that is breakable. The container 47 is filled with the second reagent 46, and the opening of the container 47 is sealed by the sheet member 48. The second reagent holding part 45 is disposed in the second accommodating part 32 in a posture in which the sheet member 48 faces downward. Accordingly, the sheet member 48 faces the protrusion 34 in the second accommodating part 32.

The pressing force applied from the second pressing operation part 12 to the second reagent holding part 45 acts in a direction of pushing down the second reagent holding part 45 downwardly, whereby the sheet member 48 is pressed against the protrusion 34. The sheet member 48 is pressed against the protrusion 34 to break the sheet member 48. The sheet member 48 is broken, and thus the second reagent 46 is supplied to the assay strip 1 through the flow channel formed by the opening 33 at the bottom of the second accommodating part 32 and the flow channel forming part 35.

As shown in FIG. 5, a gap (clearance) D corresponding to the flow channel for the second reagent 46 is formed between a back surface 36 of the flow channel forming part 35 of the multifunctional member 30 and the carrier 2 of the assay strip 1. The gap D is, for example, in the range of 0.01 mm to 1 mm. The second reagent 46 flows out from the opening 33 at the bottom of the second accommodating part 32 toward the carrier 2, and the second reagent 46 that has flowed out flows through the flow channel formed by the gap D and reaches at least above the assay region L1. The second reagent 46 that has reached the assay region L1 infiltrates the assay region L1 from the flow channel.

An absorption pad 6, which is described later, is disposed at an end part on the downstream side of the assay strip 1. As shown in FIG. 3, in the case main body 20, a support part 22 that supports the end part of the assay strip 1 including the absorption pad 6 is formed at a position facing the absorption pad 6. A second accommodating part 32 of the multifunctional member 30 is disposed above the absorption pad 6. The support part 22 also supports the multifunctional member 30 via the absorption pad 6. In addition, in the case main body 20, a support part 21 that supports a central part of the assay strip 1 is formed.

<Assay Strip>

The assay strip 1 includes a carrier 2, a liquid feeding pad 4, and an absorption pad 6. Then, the carrier 2 is fixedly supported on a back pressure-sensitive adhesive sheet 7.

(Carrier)

The carrier 2 is a porous insoluble carrier for developing a sample, and includes an assay region L1, a control region L2, and a color development region L3. In addition, the carrier 2 includes a label holding pad 3. The label holding pad 3 constitutes a spotting region on which the sample is spotted from dropping port 16. The color development region L3 is disposed on the downstream side of the assay region L1 in a case where the direction toward the assay region L1 with respect to the spotting region is the downstream side of the carrier 2. In the present example, the assay region L1, the control region L2, and the color development region L3 are line-shaped regions extending in a direction perpendicular to the development direction of the sample in the carrier 2.

In FIG. 3 to FIG. 5, a state in which the assay region L1, the control region L2, and the color development region L3 are expressed as lines is shown, but these are not always expressed. Details are described later, but before developing the sample 50 (see FIG. 6), the first reagent 41 (see FIG. 4 and FIG. 5), and the second reagent 46 (see FIG. 4 and FIG. 5), the colors of the assay region L1 and the control region L2 are substantially the same as the color of the carrier 2, and thus the assay region L1 and the control region L2 cannot be clearly visually recognized at this stage. The assay region L1 is expressed as a line by the increase of the color optical density in a case where the sample 50 is developed and the developed sample 50 is positive. In the present example, the color of the carrier 2 is close to white color. Since the color development of the assay region L1 is amplified by silver amplification, which is described later, the assay region L1 develops a black color.

The control region L2 is also expressed as a line by the increase of the color optical density in a case where the sample 50 is developed. Accordingly, the control region L2 becomes visible. Since the color development of the control region L2 is also subjected to silver amplification, the control region L2 also develops a black color.

On the other hand, only the color development region L3 is expressed and visible as a blackish dark green color (hereinafter, referred to as a dark green color) line even in a stage before the first reagent 41 is developed. However, the color development region L3 is expressed as an orange color line by changing a dark green color to an orange color in a case where the first reagent 41 is developed.

As the carrier 2, for example, a porous material such as a nitrocellulose membrane can be used. In addition, the back pressure-sensitive adhesive sheet 7 on which the carrier 2 is fixed is a sheet-shaped substrate having a pressure-sensitive adhesive surface to which the carrier 2 is attached.

(Carrier—Label Holding Pad)

Figure 6:
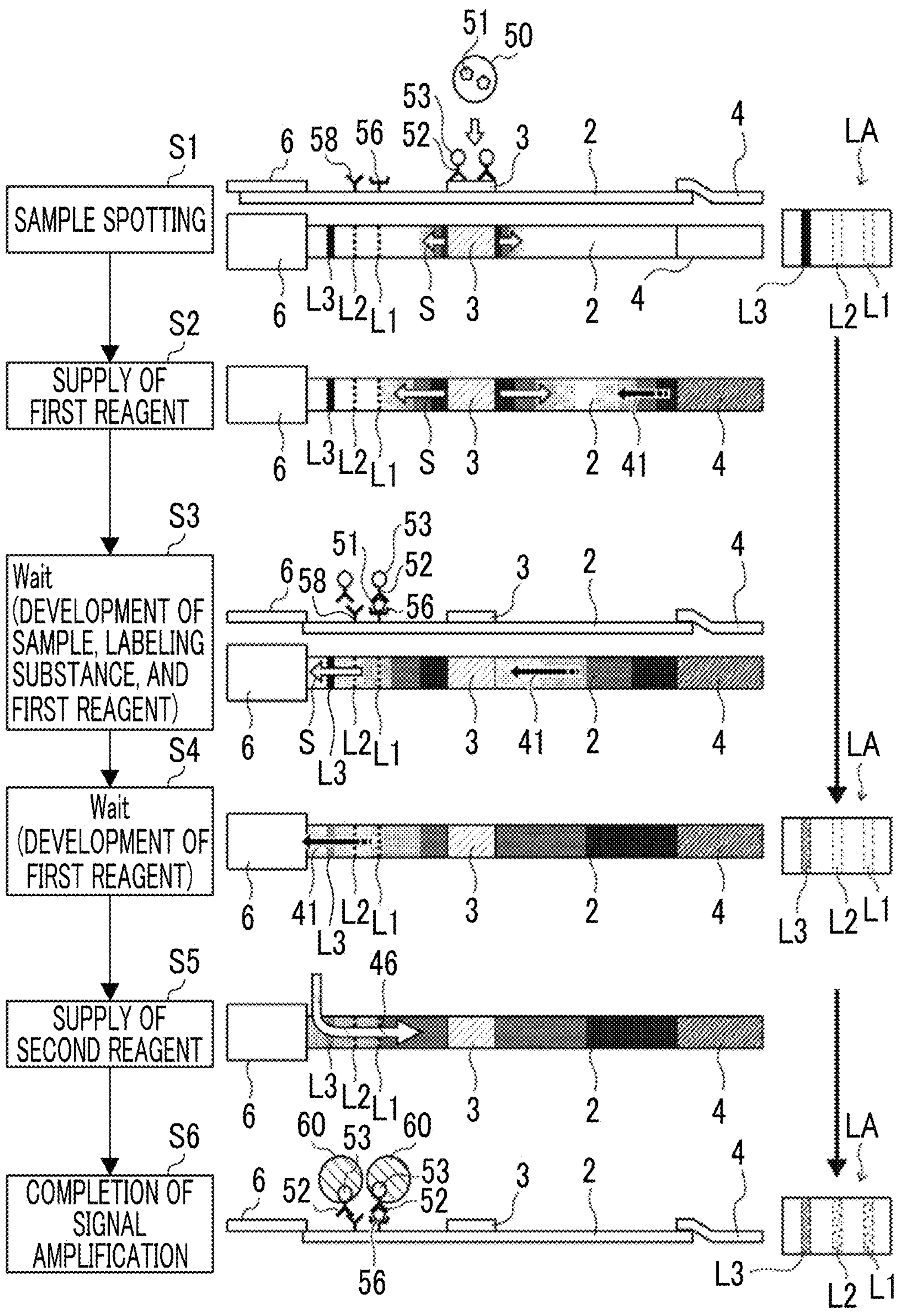
FIG. 6 is an explanatory diagram of an immunochromatographic method.

As shown in FIG. 6, a labeling substance 53 is fixed to the label holding pad 3. The labeling substance 53 is modified with the first binding substance 52 that specifically binds to the test substance 51 contained in the sample 50. The label holding pad 3 is fixed on the carrier 2 at a position facing the dropping port 16 (see FIG. 3) of the cover member 10. Therefore, the sample 50 is added dropwise onto the label holding pad 3 from the dropping port 16. Therefore, the label holding pad 3 corresponds to a spotting region on which the sample 50 is spotted.

The label holding pad 3 is fixed at a substantially center position in the longitudinal direction of the carrier 2. As the labeling substance 53, it is possible to use, for example, a gold colloidal particle having a diameter of 50 nm (EM. GC50, manufactured by BBI Solutions). The labeling substance 53 is not limited to the gold colloid, and a metal sulfide that can be used in a general chromatographic method, a coloring particle that are used in an immunoagglutination reaction, or the like can be used, where a metal colloid is particularly preferable. Examples of the metal colloid include a gold colloid, a silver colloid, a platinum colloid, an iron colloid, an aluminum hydroxide colloid, and a composite colloid thereof. In particular, at an appropriate particle diameter, a gold colloid is preferable since it exhibits a red color, a silver colloid is preferable since it exhibits a yellow color, the gold colloid is most preferable among them.

(Carrier—Assay Region)

As shown in FIG. 6, the assay region L1 includes a second binding substance 56 that specifically binds to the test substance 51 and captures the test substance 51. In the assay region L1, in a case where the test substance 51 is captured by binding the second binding substance 56 to the test substance 51, the first binding substance 52 bound to the test substance 51 and the labeling substance 53 are captured. In a case where the test substance 51 is included in the sample 50, the test substance 51 and the labeling substance 53 are captured in the assay region L1, and thus the color optical density in the assay region L1 is increased to be not less than a preset reference. The assay region L1 is a region for confirming the presence or absence of the test substance 51 by a labeling signal from the labeling substance 53 captured via the test substance 51.

(Carrier—Control Region)

The control region L2 includes a third binding substance 58 that specifically binds to the first binding substance 52, and captures the labeling substance 53 via the first binding substance 52. In a case where the sample 50 is spotted on the label holding pad 3, the labeling substance 53 that is not bound to the test substance 51 among the labeling substances 53 modified with the first binding substance 52 is also developed in the carrier 2 toward the assay region L1 together with the sample 50. The labeling substance 53 that is not bound to the test substance 51 passes through the assay region L1 without being captured by the assay region L1. The labeling substance 53 that has passed through the assay region L1 is captured in the control region L2 via the first binding substance 52 by binding the first binding substance

52 to the third binding substance 58. The labeling substance 53 is captured in the control region L2, and thus the color optical density in the control region L2 is increased to be not less than a preset reference. The control region L2 is a region for confirming the completion of the development of the sample 50 by the labeling signal from the labeling substance 53 captured via the first binding substance 52. Therefore, the control region L2 may be referred to as a confirmation region.

(Carrier—Color Development Region)

The color development region L3 contains a substance whose color development state changes by reacting with the first reagent 41. The color development region L3 indicates that the first reagent 41 has been developed to that region by reacting with the first reagent 41 to develop a color or change a color. For example, in a case where a mixed aqueous solution of an iron nitrate aqueous solution and citric acid (manufactured by Fujifilm Wako Pure Chemical Corporation, 038-06925) is used as the first reagent 41, an aspect in which the color development region L3 is constituted of a color reagent immobilization line on which Bromocresol Green (manufactured by FUJIFILM Wako Pure Chemical Corporation) has been immobilized in a line shape is preferable. This aspect is the aspect of the color development region L3 of the present example. As described above, the color development region L3 of the present example is dark green color before reacting with the first reagent 41, and the dark green color is changed to an orange color in a case where the first reagent 41 reaches the color development region L3. The color development region L3 is sometimes referred to as an amplification index region because the timing of supplying the second reagent 46 after the first reagent 41 is developed is indicated by changing the color development state.

In addition, the color development region L3 is disposed with a preset interval (see the interval T in FIG. 12, FIG. 13 and FIG. 14) from the assay region L1. The color development region L3 is a region that is optically distinguishable from other regions regardless of whether the sample is positive or negative. This color development region L3 is an example of the index region in the present disclosure, and is used as an index for specifying the position of the assay region L1 as described later.

(Forming Method of an Assay Region, a Control Region, and a Color Development Region)

Figure 7:
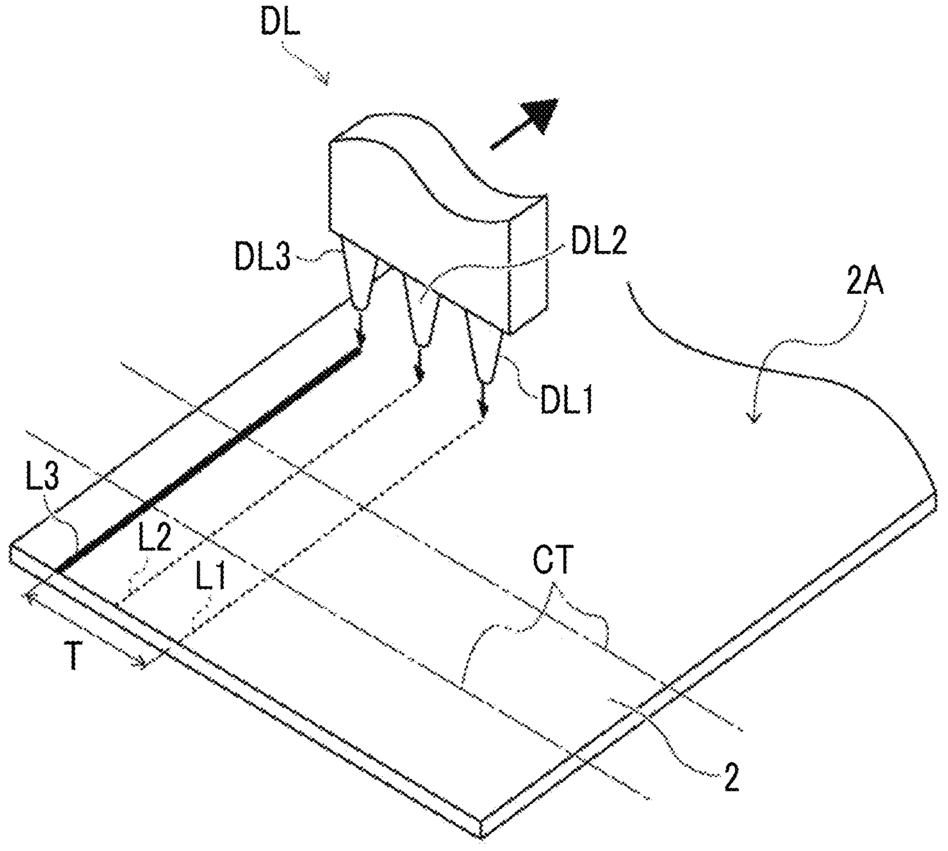
FIG. 7 is a perspective view showing an example of a manufacturing method of a carrier according to the present disclosure.

These assay region L1, control region L2, and color development region L3 are formed by coating when the carrier 2 is manufactured. Specifically, as shown in FIG. 7, a sheet material 2A for forming the carrier 2 is coated in a line shape with a material containing a substance for forming an assay region L1, a control region L2, and a color development region L3.

At this time, the assay region L1, the control region L2, and the color development region L3 are formed by coating using, as an example, a coating device (so-called dispenser) DL or the like. In the coating device DL, as outlet for discharging a coating liquid, for example, three outlets DL1, DL2, and DL3 are disposed with preset intervals. A coating liquid for forming each of the assay region L1, the control region L2, and the color development region L3 is discharged from each of the outlets DL1, DL2, and DL3. In addition, the coating device DL discharges these coating liquids while linearly moving in a direction intersecting the arrangement direction of the outlets DL1, DL2, and DL3, whereby the assay region L1, the control region L2, and the color development region L3, which have line shape are formed on the sheet material 2A. Accordingly, the interval T between the assay region L1 and the color development region L3 is determined.

After that, the sheet material 2A is cut into a predetermined width by a cut line CT to manufacture a strip-shaped carrier 2. In this way, the carrier 2 is assembled to the cartridge 100 after the assay region L1, the control region L2, and the color development region L3 are formed.

(Binding Substance)

The first binding substance 52 that modifies the labeling substance 53 shown in FIG. 6 and specifically binds to the test substance 51 is a substance that specifically binds to the test substance, for example, in a case where the test substance is an antigen, an antibody against the antigen, in a case where the test substance is an antibody, an antigen against the antibody, in a case where the test substance is a protein or a low-molecular-weight compound, an aptamer against the protein or the low-molecular-weight compound, or the like.

The second binding substance 56 that is fixed in the assay region L1 and specifically binds to the test substance 51 is a substance that specifically binds to the test substance, for example, in a case where the test substance is an antigen, an antibody against the antigen, in a case where the test substance is an antibody, an antigen against the antibody, in a case where the test substance is a protein or a low-molecular-weight compound, an aptamer against the protein or the low-molecular-weight compound, or the like. The first binding substance 52 and the second binding substance 56 may be the same as or different from each other.

The third binding substance 58 that specifically binds to the first binding substance 52 may be the test substance 51 itself or may be a compound having a site recognized by the first binding substance 52. Examples thereof include a compound obtained by binding a derivative of the test substance 51 to a protein, and the like.

For example, in a case where the test substance 51 is an influenza A virus or a biomarker thereof, an anti-influenza A monoclonal antibody (Anti-Influenza A SPTN-5 7307, manufactured by Medix Biochemica) can be used as the first binding substance 52 and the second binding substance 56, and an anti-mouse IgG antibody (anti-mouse IgG (H+L), rabbit F(ab')2, product number 566-70621, manufactured by FUJIFILM Wako Pure Chemical Corporation) can be used as the third binding substance 58.

(Liquid Feeding Pad)

The liquid feeding pad 4 is disposed in contact with one end of the carrier 2 and the first reagent 41 is fed to the carrier 2 from the upstream side of the spotting region (constituted of the label holding pad 3). As shown in FIG. 4A, in the liquid feeding pad 4, in a case where the first pressing operation part 11 is pressed, one end of the liquid feeding pad 4 is immersed in the first reagent holding part 40. The liquid feeding pad 4 is formed of a porous material and absorbs the first reagent 41, and the absorbed first reagent 41 is fed to the carrier 2 by a capillary action.

(Absorption Pad)

The absorption pad 6 is disposed in contact with the other end of the carrier 2 and absorbs the sample 50, the first reagent 41, and the second reagent 46, which are developed on the carrier 2. The absorption pad 6 is also formed of a porous material.

<Amplifying Liquid>

In the present embodiment, the first reagent 41 and the second reagent 46 are amplifying liquids that amplify the color development in the assay region L1 and the control region L2 by reacting with each other. In a case where a metal-based labeling substance such as a gold colloid is used as the labeling substance 53 as in the present example, for example, silver amplification is used as a method of amplifying the labeling signal of the labeling substance 53. The first reagent 41 and the second reagent 46 are, as an example, amplifying liquids used for silver amplification, and the reaction between the first reagent 41 and the second reagent 46 using the labeling substance 53 as a catalyst is an amplification reaction. By the amplification reaction, silver particles 60 having a particle diameter relatively larger than that of the labeling substance 53 are generated.

More specifically, in the present example, the first reagent 41 is a reducing agent that reduces silver ions, and the second reagent 46 is a silver ion. In a case where the first reagent 41, which is a reducing agent, and the second reagent 46, which is a silver ion, are brought into contact with the labeling substance 53, silver particles (see FIG. 6) are generated, and the generated silver particles deposits on the labeling substance 53 using the labeling substance 53 as a nucleus. By depositing the silver particles on the labeling substance 53, silver particles 60 having a particle diameter larger than that of the labeling substance 53 (see FIG. 6) are generated. Accordingly, the labeling signal issued by the labeling substance 53 is amplified, and as a result, the color development of the labeling substance 53 is amplified in the assay region L1 and the control region L2.

(First Reagent)

As the reducing agent as the first reagent 41, any inorganic or organic material or a mixture thereof can be used as long as the silver ion used as the second reagent 46 can be reduced to silver. Preferred examples of the inorganic reducing agent include a reducing metal salt and a reducing metal complex salt, of which the atomic valence is capable of being changed with a metal ion such as $Fe^{2+}$, $V^{2+}$, or $Ti^{3+}$. In a case where an inorganic reducing agent is used, it is necessary to remove or detoxify oxidized ions by complexing or reducing the oxidized ions. For example, in a system in which $Fe^{2+}$ is used as the reducing agent, a complex of $Fe^{3+}$, which is an oxide, is formed using citric acid or ethylenediaminetetraacetic acid (EDTA), which enables the detoxification of the oxidized ions. In the present system, such an inorganic reducing agent is preferably used, and a metal salt of $Fe^{2+}$ is more preferably used.

It is also possible to use a developing agent used in a light-sensitive silver halide photographic material of a wet-type (for example, methyl gallate, hydroquinone, substituted hydroquinone, 3-pyrazolidones, p-aminophenols, p-phenylenediamines, hindered phenols, amidoximes, azines, catechols, pyrogallols, ascorbic acid (or a derivative thereof), and leuco dyes), and other materials obvious to those who are skilled in the related art in the present field, for example, a material described in U.S. Pat. No. 6,020,117A.

As the reducing agent, an ascorbic acid reducing agent is also preferable. The useful ascorbic acid reducing agent includes ascorbic acid, an analogue thereof, an isomer thereof, and a derivative thereof. Preferred examples thereof include D- or L-ascorbic acid and a sugar derivative thereof (for example, γ-lactoascorbic acid, glucoascorbic acid, fucoascorbic acid, glucoheptoascorbic acid, or maltoascorbic acid), a sodium salt of ascorbic acid, a potassium salt of ascorbic acid, isoascorbic acid (or L-erythroascorbic acid), a salt thereof (for example, an alkali metal salt, an ammonium salt, or a salt known in the related technical field), ascorbic acid of the enediol type, ascorbic acid of the enaminol type, ascorbic acid of the thioenol type. Particularly, D-, L-, or D,L-ascorbic acid (and an alkali metal salt thereof) or isoascorbic acid (or an alkali metal salt thereof) is preferable, and a sodium salt is a preferred salt. A mixture of these reducing agents can be used as necessary.

(Second Reagent)

The solution containing silver ions, which is used as the second reagent 46, is preferably a solution obtained by dissolving a silver ion-containing compound in a solvent. As the silver ion-containing compound, an organic silver salt, an inorganic silver salt, or a silver complex can be used. An inorganic silver salt or a silver complex is preferable.

As the inorganic silver salt, it is possible to use a silver ion-containing compound having a high solubility in solvents such as water, and examples thereof include silver nitrate, silver acetate, silver lactate, silver butyrate, and silver thiosulfate. Silver nitrate is particularly preferable. The silver complex is preferably a silver complex in which silver is coordinated with a ligand having a water-soluble group such as a hydroxyl group or a sulfone group, and examples thereof include silver hydroxythioether.

<Immunochromatographic Method>

An immunochromatographic method is described with reference to FIG. 6. Here, a case where the sample 50 includes the test substance 51, that is, on the premise that the sample 50 is positive is described. In FIG. 6, a side view and a plan view of the carrier 2 are shown in the center column, a step in the immunochromatographic method is described in the left column, and an enlarged view of the observation region LA is further described in the right column. The enlarged view of the observation region LA shows a state in which the color of the color development region L3 changes from dark green color to orange color before and after the development of the first reagent 41.

In an initial state before the sample 50 is spotted, the colors of the assay region L1 and the control region L2 are substantially the same as the color of the carrier 2 (close to white color in the present embodiment), and thus the assay region L1 and the control region L2 is not clearly visible. On the other hand, the color development region L3 is expressed as a dark green line even at this stage and is visible.

First, the sample 50 is spotted on the label holding pad 3 which is the spotting region (Step S1). The test substance 51 in the sample 50 spotted on the label holding pad 3, specifically binds to the first binding substance 52 that modifies the labeling substance 53 contained in the label holding pad 3. The sample 50 is developed on the downstream side from the label holding pad 3 in the carrier 2 by the capillary action in the carrier 2. A part of the sample 50 is also developed on the upstream side.

In a case where the developed sample 50 is positive, the assay region L1 develops a black color because of the amplification action of the first reagent 41 and the second reagent 46. Accordingly, the assay region L1 is expressed as a line. However, the assay region L1 is not expressed as a line in a case where the sample 50 is negative. In a case where the sample 50 is developed, the control region L2 also develops a black color because of the amplification action of the first reagent 41 and the second reagent 46. Accordingly, the control region L2 is expressed as a line. In addition, in the present example, in a state without the amplification action of the first reagent 41 and the second reagent 46, the color development state of these regions do not change to the extent that they are visible.

Next, the first reagent 41 is supplied (Step S2). The first reagent 41 is supplied from the liquid feeding pad 4 side. The first reagent 41 is supplied to the carrier 2 through the liquid feeding pad 4 and is developed on the downstream side.

After that, the process waits until the first reagent 41 is developed on the upstream side (Step S3 and Step S4). “Wait” shown in FIG. 6 means an action of waiting. The first reagent 41 is gradually developed on the downstream side, and the sample 50 to be developed from the label holding pad 3 and the labeling substance 53 modified with the first binding substance 52 are developed on the upstream side to be pushed by the first reagent 41 (Step S3).

The test substance 51 in the sample 50 that has been developed on the downstream side and has reached the assay region L1 is captured by the second binding substance 56 in the assay region L1. That is, the labeling substance 53 bound via the test substance 51 and the first binding substance 52 is captured in the assay region L1. On the other hand, the labeling substance 53 that is not bound to the test substance 51 passes through the assay region L1 without being captured and is captured by the third binding substance 58 in the control region L2.

In a case where the development of the first reagent 41 proceeds and the first reagent 41 reaches the color development region L3 (Step S4), the color development region L3 reacts with the first reagent 41 to change the color development state. In the present example, the color development region L3 is dark green color before reacting with the first reagent 41, and the dark green color is changed to an orange color by reacting with the first reagent 41.

After the first reagent 41 is sufficiently developed, the second reagent 46 is supplied to the carrier 2 (Step S5). The second reagent 46 is supplied to the carrier 2 from the downstream side of the color development region L3 and is developed on the upstream side. Here, the first reagent 41 is a first amplifying liquid containing a reducing agent that reduces silver ions, and the second reagent 46 is a second amplifying liquid containing silver ions. By reacting the first amplifying liquid with the second amplifying liquid, the silver particles 60 are generated using the gold colloidal particles that are the labeling substance 53 as a catalyst. Accordingly, the labeling signal is amplified (Step S6).

In a case where the sample is positive, the assay region L1 develops a black color because the labeling signal is amplified by the action of the first reagent 41 and the second reagent 46. The control region L2 develops a black color because the labeling signal is amplified regardless of whether or not the sample is positive.

<Immunochromatographic Assay Apparatus>

As shown in FIG. 1, the assay apparatus 110 includes a housing 111, and the housing 111 includes a cartridge loading part 112 in which the cartridge 100 is attachably and detachably loaded. As an example, an opening for inserting the cartridge 100 into the housing 111 and an opening and closing lid 112*a* for opening and closing this opening are provided on the front surface of the housing 111. The opening and closing lid 112*a* is opened when the cartridge 100 is loaded, the cartridge 100 is inserted into the housing 111, and the opening and closing lid 112*a* is closed after the cartridge 100 has been loaded into the cartridge loading part 112. The assay is performed in a state where the opening and closing lid 112*a* is closed.

In addition, a power switch 113 is provided on the front surface of the housing 111, and a monitor 119 is provided on the upper surface of the housing 111. A determination result, an error message, and the like are displayed on the monitor 119. As an example, the monitor 119 is a touch panel monitor, and various operation screens are displayed. Through the operation screen, the user can input a start instruction of processing and an operation instruction such as selection of an assay procedure. The power switch 113, the monitor 119, or the like may not be provided in the housing 111. In this case, for example, the assay apparatus 110 is connected to a computer such as a personal computer, and the assay apparatus 110 is controlled by the computer. Then, an operation instruction including turning on and off of the power of the assay apparatus 110 is input from the computer, and the operation screen, the determination result, and the like are displayed on the monitor of the computer.

In the assay apparatus 110, as an example, a cartridge 100 is loaded in a state in which the spotting of the sample on the carrier 2 and the supply of the first reagent 41 and the second reagent 46 to the carrier 2 are started. That is, in the present example, the pressing operation of the first pressing operation part 11 and the second pressing operation part 12 is performed by the user before the cartridge 100 is loaded into the assay apparatus 110. Accordingly, the cartridge 100 is in the state shown in FIG. 4B, and the cartridge 100 is loaded into the assay apparatus 110 in this state. The assay apparatus 110 detects a color development state of the assay region L1 of the loaded cartridge 100, and presents the result of whether the sample is positive or negative. In a case where a plurality of samples are assayed, the cartridge 100 for each sample is loaded one by one into the assay apparatus 110.

Figure 8:
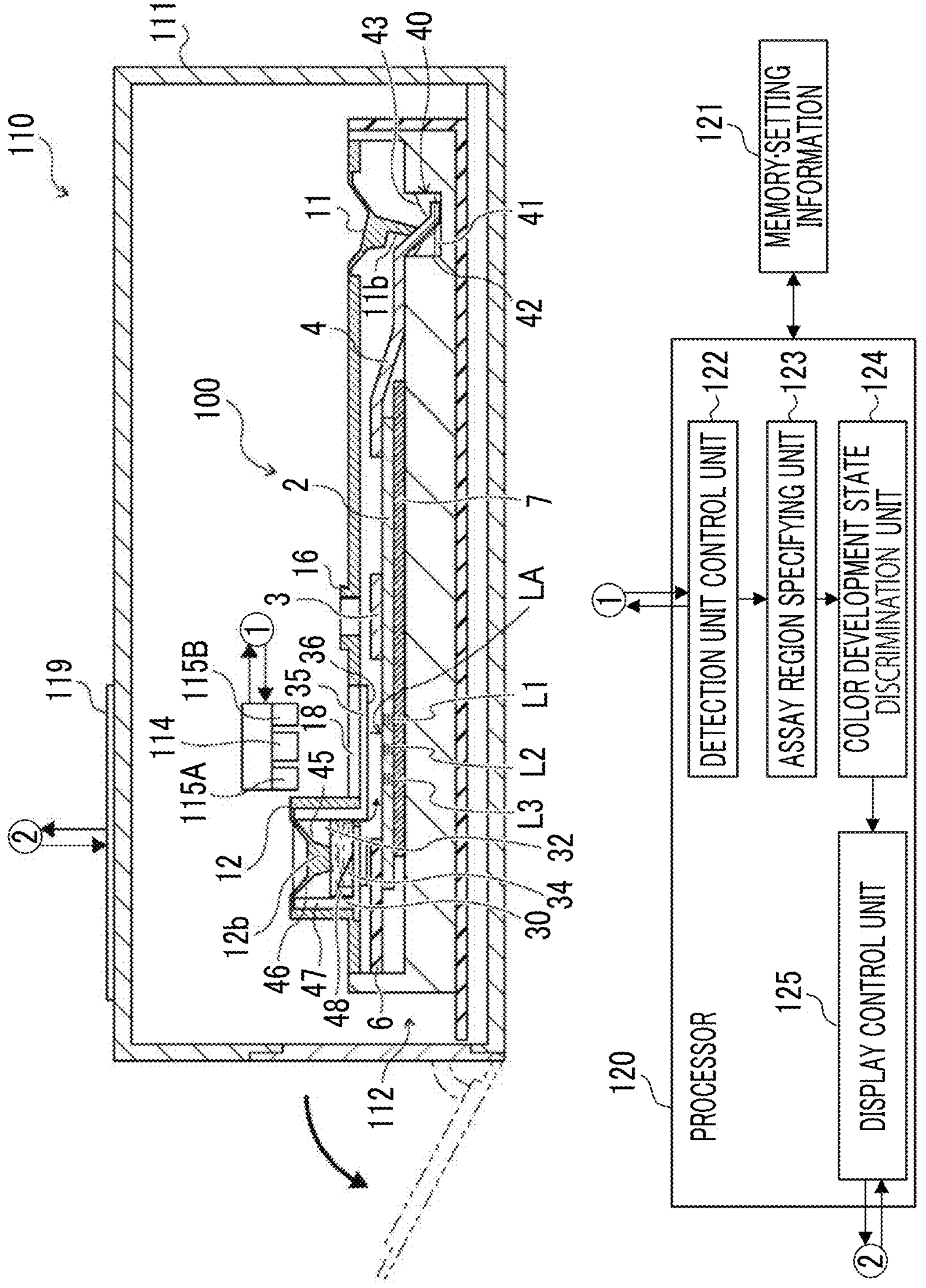
FIG. 8 is a partially broken side view of the assay apparatus according to the present disclosure.

As shown in FIG. 8, the assay apparatus 110 includes the loading part 112, the detection unit 114, the light source 115, the processor 120, and a memory 121 in the housing 111. In FIG. 8, the processor 120 and the memory 121 are illustrated outside the housing 111 of the assay apparatus 110, but this is a schematic diagram, and the processor 120 and the memory 121 are actually disposed inside the housing 111.

(Detection Unit)

The detection unit 114 optically detects the color development state of the assay region L1, the control region L2, and the color development region L3, and outputs a detection signal indicating the color development state to the processor 120. The detection unit 114 includes, for example, an image sensor such as a complementary metal oxide semiconductor (CMOS) image sensor and a charge coupled device (CCD) image sensor and an imaging unit that images the observation region LA including the assay region L1, the control region L2, and the color development region L3. Then, the image including the observation region LA, which is imaged is output from the detection unit 114 to the processor 120. Here, “imaging the observation region LA” includes not only an aspect of imaging only the observation region LA but also an aspect of imaging the observation region LA and its peripherals. Hereinafter, the aspect of imaging the observation region LA and the peripherals is described. In the following description, the image imaged by the detection unit 114 will be referred to as an “captured image”, and an image trimmed from the captured image and including only the observation region LA is referred to as an “observation image”.

The detection unit 114 is disposed at a position directly facing the observation region LA in a state where the cartridge 100 is loaded in the assay apparatus 110.

(Light Source)

A light source 115 such as a light emitting diode that illuminates the observation region LA on the carrier 2, which includes the assay region L1, the control region L2, and the color development region L3 at the time of imaging of the detection unit 114, is provided on the side of the detection unit 114. The light source 115 of the present example includes a first light source 115A that emits green color monochromatic light and a second light source 115B that emits red color monochromatic light.

The first light source 115A is disposed on the side of the detection unit 114, and the second light source 115B is disposed on the side of the detection unit 114 and on the side opposite to the first light source 115A. In FIG. 8, the first light source 115A, the detection unit 114, and the second light source 115B are disposed side by side along the longitudinal direction of the carrier 2, but the first light source 115A, the detection unit 114, and the second light source 115B may be disposed side by side along the width direction orthogonal to the longitudinal direction of the carrier 2. The first light source 115A and the second light source 115B may be disposed one by one on each of both sides of the detection unit 114. In the following description, the green color light emitted by the first light source 115A may be referred to as G light, and the red color light emitted by the second light source 115B may be referred to as R light.

As shown in FIG. 6, the color development region L3 of the present example is dark green color before reacting with the first reagent 41, and changes to orange color when the first reagent 41 reaches the color development region L3. In the technology of the present disclosure, dark green color is an example of a first color before color change, and orange is an example of a second color after color change. The first light source 115A emits G light in which the amount of the reflected light in a case where the color development region L3 of the dark green color, which is an example of the first color, is irradiated is larger as compared with a case where the color development region L3 of the orange color, which is an example of the second color, is irradiated. This is because the orange color absorbs more G light than the dark green color.

On the other hand, the second light source 115B emits R light in which the amount of the reflected light in a case where the color development region L3 of the orange color, which is an example of the second color, is irradiated is larger as compared with a case where the color development region L3 of the dark green color, which is an example of the first color, is irradiated. This is because the dark green color absorbs more R light than the orange color.

The G light is an example of the first monochromatic light, and the first light source 115A is an example of the first monochromatic light source. In addition, the R light is an example of the second monochromatic light, and the second light source 115B is an example of the second monochromatic light source.

(Processor)

The processor 120 integrally controls each part of the assay apparatus 110. An example of the processor 120 is a Central Processing Unit (CPU) that performs various types of control by executing a program. The CPU functions as a control unit having a detection unit control unit 122, an assay region specifying unit 123, a color development state discrimination unit 124, and a display control unit 125 by executing a program. The memory 121 is an example of a memory connected to or built in the CPU as the processor 120. For example, a control program is stored in the memory 121. The processor 120 is realized by the CPU executing a control program.

In addition to the control program, the memory 121 stores setting information that is preset in order for the processor 120 to perform various types of control. As the setting information, information necessary for the color development state discrimination unit 124 to discriminate a change in the color development state is recorded. The setting information also includes an interval T between the color development region L3 and the assay region L1 (see FIG. 12, FIG. 13, and FIG. 14).

The detection unit control unit 122 controls the imaging timing of the observation region LA by the detection unit 114 by transmitting a control signal to the detection unit 114. In addition, the detection unit control unit 122 acquires the captured image imaged by the detection unit 114 and outputs the captured image to the assay region specifying unit 123. As described above, the captured image is an image including the observation region LA. The detection unit control unit 122 illuminates the observation region LA with the G light by turning on only the first light source 115A, and operates the detection unit 114 in that state to image the observation region LA under the illumination of the G light. Accordingly, the detection unit control unit 122 acquires the captured image including the observation image PG (see FIG. 12) imaged under the illumination of the G light. In addition, the detection unit control unit 122 illuminates the observation region LA with the R light by turning on only the second light source 115B, and operates the detection unit 114 in that state to image the observation region LA under the illumination of the R light. Accordingly, the detection unit control unit 122 acquires the captured image including the observation image PR (see FIG. 12) imaged under the illumination of the R light. Hereinafter, the observation image PG and the observation image PR are also referred to as a G light observation image PG and a R light observation image PR, respectively.

The assay region specifying unit 123 acquires the observation images PG and PR by trimming the observation images PG and PR including the observation region LA from the two captured images acquired under the respective illuminations of the G light and the R light. Then, the assay region specifying unit 123 executes a processing of detecting the position of the color development region L3 as the index region from the acquired observation images PG and PR, and specifying the position of the assay region L1 with reference to the position of the detected color development region L3. In the technology of the present disclosure, the observation image PG is an example of the first image, and the observation image PR is an example of the second image.

The color development state discrimination unit 124 executes color development state discrimination processing of discriminating the color development state of the assay region L1 specified by the assay region specifying unit 123, by using at least one of the observation images PG and PR imaged by the detection unit 114.

The color development state discrimination processing is a processing of discriminating presence or absence of a change in the color development state of the assay region L1. In a case where the sample 50 is positive, a line is expressed in the assay region L1, and thus, in the color development state discrimination processing, presence or absence of the expression of the line in the assay region L1 is discriminated.

In a case where the color development state discrimination unit 124 discriminates that the change in the color development state in the assay region L1 is present, the processor 120 determines that the sample 50 is positive. In this case, an indication that the assay result is "positive" is displayed on the monitor 119 via the display control unit 125. In addition, in a case where the color development state discrimination unit 124 discriminates that the change in the color development state in the assay region L1 is absent, the processor 120 determines that the sample 50 is negative. In this case, an indication that the assay result is "negative" is displayed on the monitor 119 via the display control unit 125.

<Immunochromatographic Assay>

Figure 9:
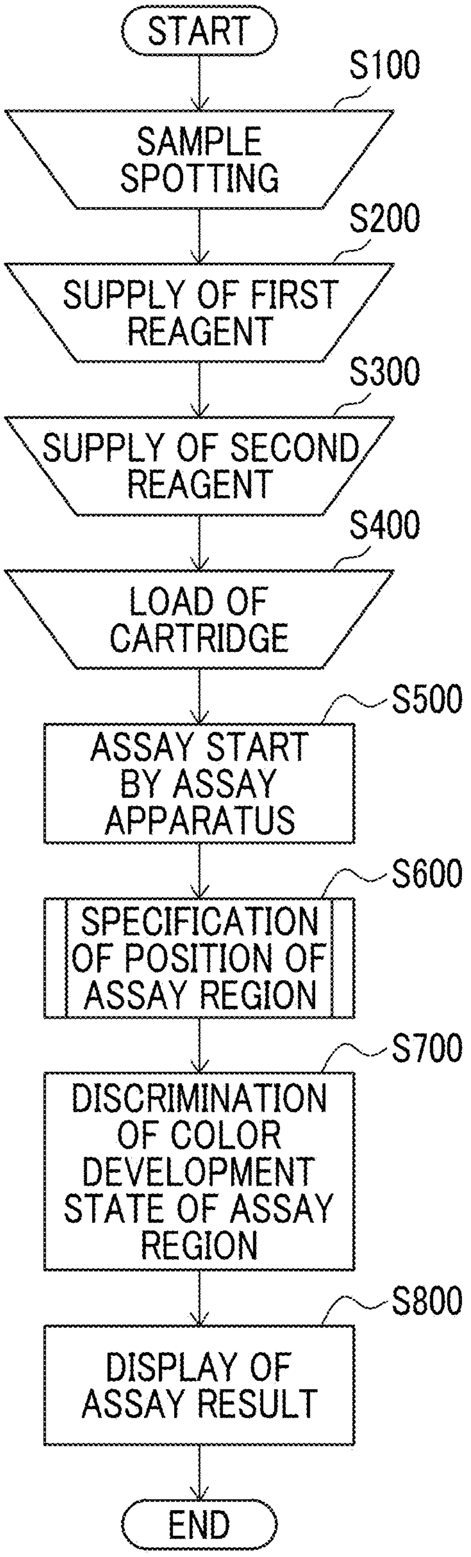
FIG. 9 is a flowchart showing an assay flow of the assay apparatus according to the present disclosure.

The assay flow of the immunochromatographic assay using the assay apparatus 110 of the present embodiment is described. First, as shown in FIG. 9, the sample 50 is added dropwise from the dropping port 16 of the cartridge 100 onto the spotting region of the carrier 2 by an user. As a result, the sample 50 is spotted onto the carrier 2 (Step S100).

Next, the first pressing operation part 11 of the cartridge 100 is pressed by the user to start supplying the first reagent 41 to the carrier 2 (Step S200).

Next, the color change of color development region L3 from dark green color to orange color is confirmed by the user, and then the second pressing operation part 12 of the cartridge 100 is pressed by the user to start supplying the second reagent 46 to the carrier 2 (Step S300).

Next, the cartridge 100 is loaded into the loading part 112 of the assay apparatus 110 by the user (Step S400).

After that, the assay for the loaded cartridge 100 is started in the assay apparatus 110 (Step S500).

In the assay for the cartridge 100, first, the processor 120 specifies the position of the assay region L1 in the observation region LA (Step S600). Details of the specifying processing of the position of the assay region L1 is described later.

Next, the processor 120 discriminates the color development state of the assay region L1 (Step S700).

Then, in a case where it is discriminated that a change in the color development state of the assay region L1 is present, the processor 120 determines that the sample 50 is positive and displays an indication that the assay result is "positive" on the monitor 119. In addition, in a case where it is discriminated that a change in the color development state of the assay region L1 is absent, the processor 120 displays an indication that the assay result is "negative" on the monitor 119 (Step S800), and terminates the assay flow.

(Specifying Processing of Assay Region)

Next, the specifying processing of the assay region L1 in the above-described Step S600 is described with reference to FIG. 10. In the specifying processing of the position of the assay region L1, the processor 120 operates the detection unit 114, the first light source 115A, and the second light source 115B to acquire the G light observation image PG (see FIG. 12) and the R light observation image PR (see FIG. 12) (Step S610). As described above, the G light observation image PG is an image of the observation region LA imaged under the illumination of the G light by the first light source 115A. The R light observation image PR is an image of the observation region LA imaged under the illumination of the R light by the second light source 115B. Details of these observation images are described later.

Next, the processor 120 detects the position of the color development region L3 as the index region by performing image recognition on the observation images PG and PR (Step S620). Details of the detection processing for the position of the color development region L3 is described later.

Next, the processor 120 specifies the position of the assay region L1 based on the position of the color development region L3 (Step S630), and terminates the specifying processing of the assay region L1. After the specifying processing of the assay region L1, the process proceeds to Step S700 of FIG. 9.

(Detection Processing of Position of Index Region)

Next, the detection processing of the position of the color development region L3 in the above-described Step S620 is described with reference to FIG. 11. In the detection processing of the position of the color development region L3, first, the processor 120 derives a difference image ΔP (see FIG. 12) between the acquired G light observation image PG and the acquired R light observation image PR (Step S621). Next, the processor 120 detects the position of the color development region L3 as the index region based on this difference image ΔP (Step S622). After the detection of the position of the color development region L3, the process proceeds to Step S630 of FIG. 10.

Figure 11:
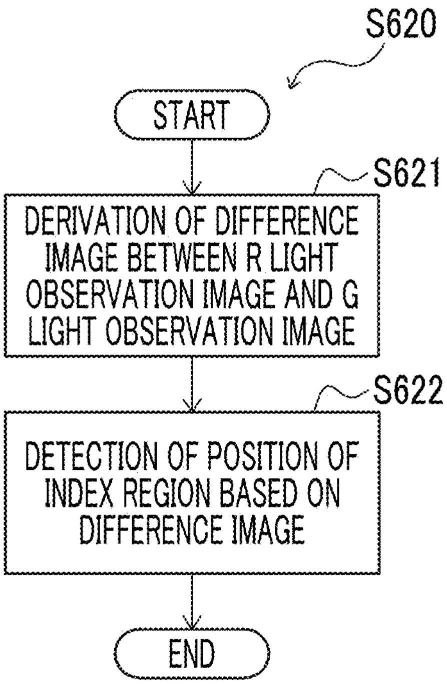
FIG. 11 is a flowchart showing a flow of a processing of detecting a position of an index region in the assay apparatus according to the present disclosure.
Figure 12:
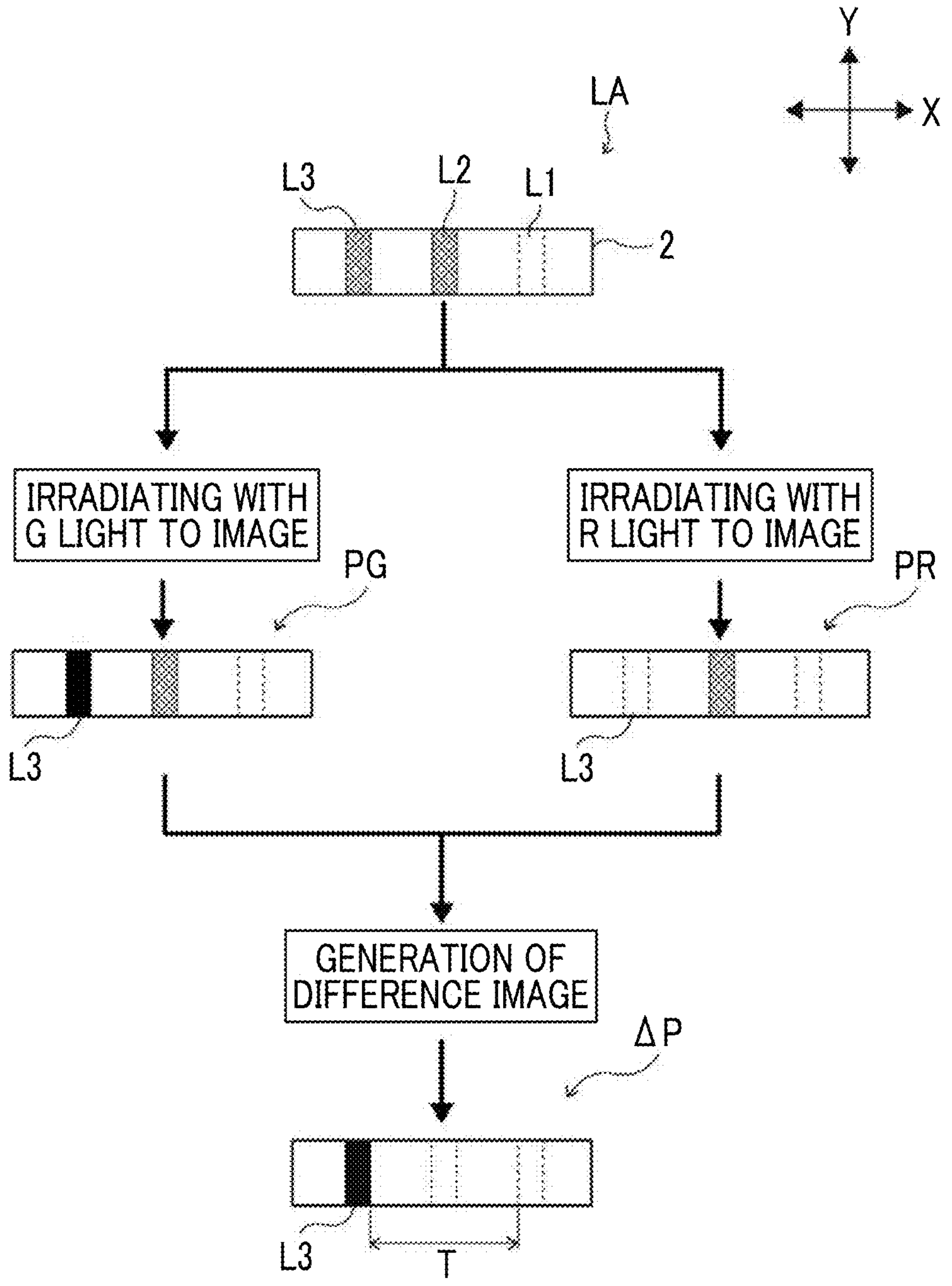
FIG. 12 is a conceptual diagram showing an observation region to be imaged by the assay apparatus according to the present disclosure, captured images of the observation region, and a difference image between two captured images.

The processing shown in FIG. 11 is conceptually described with reference to FIG. 12. FIG. 12 shows the observation region LA in a state where the cartridge 100 is loaded in the assay apparatus 110. In the present example, since the cartridge 100 is loaded into the assay apparatus 110 after the color development region L3 changes color to orange color, in the observation region LA, the color development region L3 as the index region develops orange color. On the other hand, the assay region L1 develops black color in a case where the sample 50 is positive, but does not develop color in a case where the sample 50 is negative. Therefore, in a case where the sample 50 is negative, the assay region L1 has substantially the same color as the carrier 2. In this case, since the assay region L1 has not developed color, the position of the assay region L1 cannot be specified by image recognition. Therefore, the processor 120 detects the color development region L3, which is an example of the index region, by image recognition, and specifies the position of the assay region L1 with reference to the position of the detected color development region L3.

Figure 10:
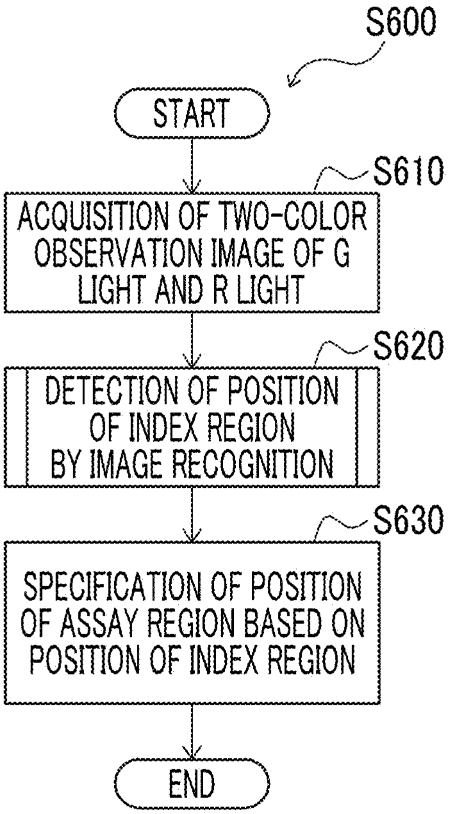
FIG. 10 is a flowchart showing a flow of a processing of specifying a position of an assay region in the assay apparatus according to the present disclosure.

As shown in FIG. 12, the G light observation image PG imaged by irradiating with the G light and the R light observation image PR imaged by irradiating with the R light are acquired by Step S610 of FIG. 10. The observation images PG and PR are monochrome images because they are both imaged by monochromatic light of G light or R light. In FIG. 12, also in the observation image PG and the observation image PR, a region corresponding to the color development region L3 on the observation region LA is shown as the color development region L3.

Since the color development region L3 is changed to orange color, in a case where the G light observation image PG and the R light observation image PR are compared with each other, the color optical density of the color development region L3 is higher in the G light observation image PG. This is because the amount of reflected light in the orange color of the R light is larger than that of the G light. Since the carrier 2 is close to white color, the amount of reflected light of the R light is large similarly to the orange color. Therefore, in the R light observation image PR, the brightness of both the backing of the carrier 2 close to white color and the color development region L3 is high, and both are difficult to distinguish from each other. On the other hand, in the G light observation image PG, in a case where the backing of the carrier 2 close to white color is compared with the color development region L3 of orange color, the amount of reflected light of G light in the backing of the carrier 2 is large, and thus the density of the color development region L3 is high. Therefore, it is easy to distinguish the color development region L3.

The difference image ΔP between the observation image PG and the observation image PR is a difference image ΔP between the observation image PG and the observation image PR shown in FIG. 12. This difference image ΔP is an image showing a density difference between the observation image PG and the observation image PR. In the observation image PG, the density in the color development region L3 is high, and the density in other portions is low. On the other hand, in the observation image PR, the densities in the color development region L3 and the other portions are similarly low. Therefore, in the difference image ΔP, only the color development region L3 remains in a distinguishable state.

Figure 13:
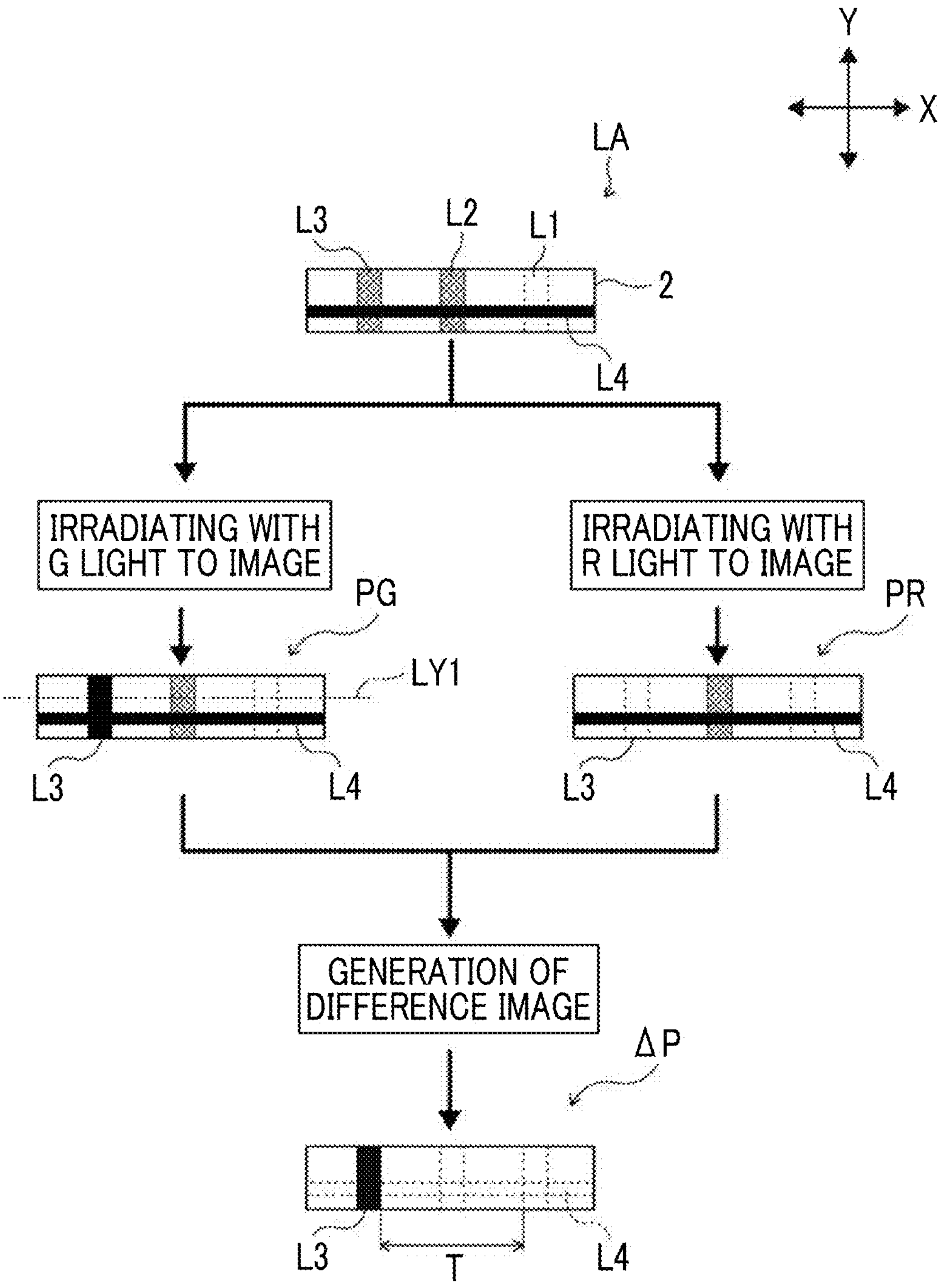
FIG. 13 is a conceptual diagram showing an observation region in a case where noise is present, an image captured in the observation region, and a difference image between two captured images.

In addition, in the present example, the reason for using the two-color observation images of the G light observation image PG and the R light observation image PR is to improve the detection accuracy of the color development region L3. That is, for example, a case where the noise region L4 is provided on the carrier 2 as shown in FIG. 13 is considered. The noise region L4 is a line-shaped region along the X direction that has developed a black color because of, for example, impurities mixed in the carrier 2. Since the noise region L4 is black, the noise region L4 is reflected in both the G light observation image PG and the R light observation image PR.

In a case where the processor 120 detects the color development region L3, a preset position of the carrier 2 in the Y direction on the G light observation image PG is searched along the X direction from the downstream side (the end part side close to the color development region L3) of the carrier 2. Then, the processor 120 detects a region having a higher density than the backing of the carrier 2 as the color development region L3. At this time, as shown in FIG. 13, in a case where the position in the Y direction searched by the processor 120 is, for example, the position LY1 that does not overlap with the noise region L4, the search is performed in the X direction to detect the color development region L3 based on the density difference between the backing of the carrier 2 and the high density region. However, in a case where the position in the Y direction searched by the processor 120 overlaps with the noise region L4, since the entire region of the noise region L4 extending in the X direction has a high density, it is difficult to distinguish from the color development region L3 based on the density difference, and the color development region L3 can not be detected.

Therefore, the color development region L3 cannot be detected only by the G light observation image PG. In addition, since the color development region L3 is not visualized in the R light observation image PR, the color development region L3 cannot be detected.

Therefore, the processor 120 detects the position of the color development region L3 by using the two-color observation images, the G light observation image PG and the R light observation image PR, and using the difference image ΔP derived from these observation images. In the difference image ΔP, since the noise region L4 visualized in both the G light observation image PG and the R light observation image PR is canceled, only the color development region L3 remains in a distinguishable state.

Figure 14:
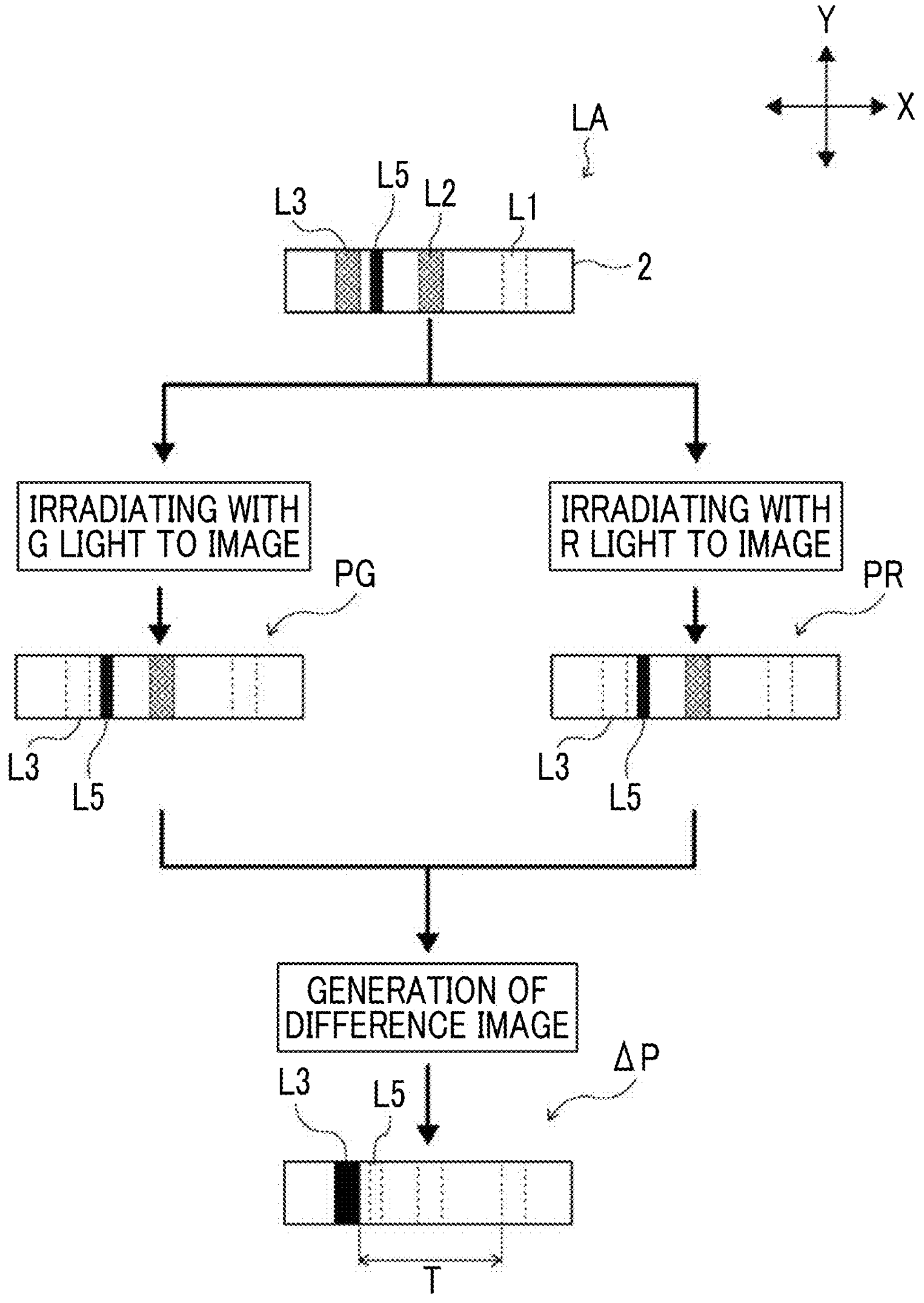
FIG. 14 is a conceptual diagram showing an observation region in a case where noise other than the noise shown in FIG. 13 is present, an image captured in the observation region, and a difference image between two captured images.

In addition, for example, a case where the noise region L5 is provided on the carrier 2 as shown in FIG. 14 is considered.

The noise region L5 is a line-shaped region along the Y direction that has developed a black color because of, for example, impurities mixed in the carrier 2. In this case, since the noise region L5 is black, the noise region L5 is reflected in both the G light observation image PG and the R light observation image PR. Therefore, in a case where there is a noise region L4, two lines of the color development region L3 and the noise region L4 are visualized in the G light observation image PG, and thus which is the color development region L3 can not be specified in only the G light observation image PG. In addition, in the R light observation image PR, the color development region L3 is not visualized, but the noise region L4 is visualized, and thus in only the R light observation image PR, the noise region L4 may be erroneously detected as the color development region L3.

Therefore, the processor 120 detects the position of the color development region L3 by using the two-color observation images, the G light observation image PG and the R light observation image PR, and using the difference image ΔP derived from these observation images. In the difference image ΔP, since the noise region L4 visualized in both the G light observation image PG and the R light observation image PR is canceled, only the color development region L3 remains in a distinguishable state.

Here, the processor 120 detects the position of the color development region L3 based on the optical density of the color development region L3 as the index region. Specifically, in the difference image ΔP, the processor 120 detects the position of the color development region L3 using the Δ optical density (OD) value, which is a difference between the optical density of the color development region L3, which is an example of the index region, and the optical density of a background region, which is the background of the color development region L3, that is, a portion other than the color development region L3.

The processor 120 compares, for example, a ΔOD value of each pixel of the difference image ΔP with a preset threshold value. Then, the processor 120 specifies a region in which the ΔOD value is not less than a preset threshold value, as the position of the color development region L3. The threshold value is, for example, 0.015 [a. u.]. In general, the density difference in which the ΔOD value is 0.015 [a. u.] or more is a density difference to the degree to be visible by human eyes. By using the ΔOD value for detecting the position of the color development region L3, the influence of individual differences in optical densities between the color development region L3 and the background region can be reduced.

In this way, the processor 120 detects the position of the color development region L3 as the index region by the image recognition using the observation image PG, the observation image PR, and the difference image ΔP derived from these. Then, the processor 120 specifies the position of the assay region L1 using the preset interval T with reference to the position of the color development region L3. In the present example, the color development region L3 and the assay region L1 are disposed with an interval T along the longitudinal direction of the carrier 2. The processor 120 obtains a position separated by the interval T from the position of the detected color development region L3 in the longitudinal direction of the carrier 2 in the difference image ΔP by a simple distance calculation and thus specifies the position as the position of the assay region L1.

<Action and Effect>

In the assay apparatus 110 of the present disclosure, the detection unit 114 as the imaging unit shown in FIG. 8 images the observation region LA on the carrier 2. The observation region LA includes the assay region L1 in which the color development state changes depending on whether the sample is positive or negative, and the color development region L3 as an example of an index region that is optically distinguishable from other regions regardless of whether the sample is positive or negative.

In the assay apparatus 110 of the present disclosure, the processor 120 detects the position of the color development region L3 as the index region from the observation images PG and PR shown in FIG. 12, which is an example of the image of the observation region LA imaged by the detection unit 114. The assay region L1 cannot be detected in a case where the sample is negative, but the color development region L3 can be optically distinguished from other regions regardless of whether the sample is positive or negative, and thus the position can be detected as compared with the assay region L1.

Since the assay region L1 is disposed with a preset interval T (see FIG. 12) from the color development region L3, in a case where the processor 120 can detect the position of the color development region L3, the position of the assay region L1 can be specified with reference to the position of the detected color development region L3.

Since the assay region L1 is not expressed in a case where the sample 50 is negative, it is difficult to detect the position of the assay region L1 by image recognition based on the optical density in a case where the sample 50 is negative. Even in this case, in a case where the position of the color development region L3 is used as a reference as described above, the position of the assay region L1 can be specified by a simple distance calculation.

In addition, even in a case where the sample 50 is positive, the change in the color development state of the assay region L1 may be very weak. In this case, in a state where the position of the assay region L1 is not specified, it is difficult to optically distinguish the change in the color development state from the noise present in the other region, and erroneous recognition is likely to occur. Even in such a case, the technology of the present disclosure may be effective. That is, according to the technology of the present disclosure, it is possible to detect the color development region L3 as an index region by image recognition based on optical density, and specify the position of the assay region L1 based on the detected color development region L3 without relying on image recognition based on optical density. Therefore, according to the technology of the present disclosure, the position of the assay region L1 can be specified even in a case where the change in the color development state is weak. In a case where the position of the assay region L1 can be specified, erroneous recognition with noise present in a region other than the assay region L1 is suppressed, and thus the possibility of detecting a weak change in the color development state in the assay region L1 is increased.

Both the assay region L1 and the color development region L3 are regions formed on the carrier 2. Therefore, the cartridge 100 is configured, for example, by assembling the case main body 20 and the carrier 2, which are separate parts. The individual difference in the misregistration between the assay region L1 and the color development region L3 is much smaller than the individual difference in the misregistration between the case main body 20 and the carrier 2.

The assay apparatus 110 of the present disclosure specifies the position of the assay region L1 with reference to the position of the color development region L3 detected from the observation images PG and PR of the observation region LA on the carrier 2, and thus even in a case where the misregistration between the case main body 20 and the carrier 2 occurs because of the individual difference of the cartridge 100, the position of the assay region L1 can be specified.

In a case where the position of the assay region L1 can be specified in this way, it is possible to suppress the occurrence of erroneous determination due to the erroneous recognition of a region other than the assay region L1 as the assay region L1.

In addition, in the assay apparatus 110 of the present disclosure, the processor 120 detects the position of the color development region L3 based on the optical density of the color development region L3 as the index region. Since the optical density can be measured regardless of a color such as red or green, it is possible to detect even in a case where the image is monochrome. Accordingly, as the light source 115, not only a white color light source but also a monochromatic light source, for example, a first light source 115A or a second light source 115B can be used.

In addition, in the assay apparatus 110 of the present disclosure, the color development region L3 in which the color development state changes by reacting with the first reagent 41 as the reagent is detected as an index region. In addition, the first reagent 41 is an amplifying liquid for amplifying a change in the color development state of the assay region L1. In a case where the amplifying liquid is used as the reagent, a region that reacts with the amplifying liquid, that is, the color development region L3 can be used as an index region.

It is not necessary to use the amplifying liquid as the reagent. That is, in the assay apparatus 110 of the present disclosure, in a case where the carrier 2 is provided with a region that reacts with not only the combination of the first reagent 41 and the color development region L3, but also some labeling substance, the region can be used as the index region.

For example, in the assay apparatus 110, the control region L2 in which the color development state changes by reacting with the labeling substance 53 may be detected as an index region. In addition to the color development region L3 and the control region L2, in a case where the carrier 2 is provided with a region that reacts with some kind of reagent, this region can be used as an index region.

In addition, as described in the above-described embodiment, in the case where the color development region L3 (an example of the index region) is dark green color (an example of the first color) before reacting with the reagent, and changes from dark green color to orange color (an example of the second color) by reacting with the reagent, the assay apparatus 110 of the present disclosure includes a first light source 115A (an example of a first monochromatic light source) and a second light source 115B (an example of a second monochromatic light source). The first light source 115A emits G light (an example of the first monochromatic light) in which the amount of the reflected light in a case where the color development region L3 of the orange color is irradiated is larger as compared with a case where the color development region L3 of the dark green color is irradiated. The second light source 115B emits R light (an example of the second monochromatic light) in which the amount of reflected light in a case where the color development region L3 of the orange color is irradiated is larger. Then, the processor 120 acquires the G light observation image PG obtained by imaging the color development region L3 of the orange color using the first light source 115A and the detection unit 114 (an example of the imaging unit), and further acquires the R light observation image PR obtained by imaging the color development region L3 of the orange color using the second light source 115B and the detection unit 114. Then, the processor 120 detects the color development region L3 based on the G light observation image PG and the R light observation image PR. Therefore, even in a case where the noise region L4 or the like is included in the observation region LA, the color development region L3 can be detected with high accuracy by using, for example, the difference image ΔP between the observation image PG and the observation image PR.

The first color and the second color of the index region shown in the above-described embodiment are examples, and other colors may be used. In this case, the first monochromatic light and the second monochromatic light are also selected according to the first color and the second color. In the above example, the first color is a dark green color and contains a green color component, and the second color is an orange color. Therefore, the first light source 115A, which is an example of the first monochromatic light source, is a green color light source, and the second light source 115B, which is an example of the second monochromatic light source, is a red color light source.

In addition, in the assay apparatus 110 of the present disclosure, the first light source 115A as the first monochromatic light source, by which the color development region L3 is irradiated, is a green color light source, and the second light source 115B as the second monochromatic light source is a red color light source. Since the wavelength of red color light is longer than that of blue color light, the energy of red light is lower. Therefore, deterioration of the observation region LA can be suppressed. Since the wavelength of the green color light is also longer than, for example, that of the blue color light, the same effect as that of the red color light can be obtained.

In addition, in the assay apparatus 110 of the present disclosure, in the cartridge 100, the assay region L1 and the color development region L3 as the index region are regions formed by coating on the carrier 2, and the carrier 2 is assembled to the case 9 after the assay region L1 and the color development region L3 are formed.

In a case where the assay region L1 and the color development region L3 are formed after the carrier 2 is assembled to the case 9, individual differences in the cartridge 100 are likely to occur in the interval between the assay region L1 and the color development region L3, or the like. Therefore, the misregistration between the assay region L1 and the color development region L3 are less likely to occur as compared with a case where the assay region L1 and the color development region L3 are formed after the carrier 2 is assembled to the case 9. Accordingly, the accuracy of specifying the position of the assay region L1 with reference to the position of the color development region L3 (an example of the index region) is improved.

In the assay apparatus 110 of the present disclosure, the control region L2 is also formed by coating on the carrier 2 before being assembled to the case 9. Therefore, the same effect can be obtained even in a case where the control region L2 is used as the index region.

Other Embodiments

In the assay apparatus 110 of the present disclosure, the first light source 115A of the green color light source and the second light source 115B of the red color light source are used as the light sources, but the embodiment of the present disclosure is not limited to these. For example, a white color light source may be used as the light source. In this case, in a case where an imaging unit capable of imaging a color image is used as the detection unit 114, the captured image imaged by the detection unit 114 and a part of the observation image thereof are color images. In this case, the processor 120 can detect the index region in the observation image by distinguishing the color instead of or in addition to the optical density. That is, the processor 120 detects the position of the index region based on the color of the index region.

For example, in a case where noise is generated because of the mixing of foreign matter or the like, it may be difficult to distinguish between the noise and the color development region L3 in the case of a monochrome image. Therefore, color-based detection may have higher detection accuracy, and the use of a color image is effective in such a case.

In addition, in the above-described embodiment, the processor 120 detects the position of the index region based on the optical density of the index region, but the present disclosure is not limited to this. For example, the processor 120 may detect the position of the index region based on the form of the index region. The form of the index region is, for example, a pattern such as a circle, a triangle, or a stripe pattern, or the like. In this way, in a case where the form of the color development region is characteristic, it is possible to detect the color development region based on the form of the color development region.

In the above-described embodiment, the position of the index region is detected using two observation images acquired by using the monochromatic light sources of two colors of G light and R light, but the position of the index region may be detected using one observation image acquired by using the monochromatic light source of one color. For example, in a case where an index region that develops a color other than the green color, such as the color development region L3 of the orange color, is detected as in the above-described embodiment, the index region can be detected even by using only the G light observation image PG. Accordingly, it is possible to specify the position of the assay region L1.

In the above-described embodiment, the color of the carrier 2, that is, the background color of the assay region L1, the control region L2, and the color development region L3 has been described as an example of a color close to a white color, but the color of the carrier 2 may be another color. The color of the carrier 2 may be a color that is distinguishable from the colors of the assay region L1, the control region L2, and the color development region L3 in a case where these develop a color.

In addition, in the above-described embodiment, the color development region L3 is detected using only the observation image of the color development region L3 after the color change, but the color development region L3 may be detected using the observation image of the color development region L3 before the color change. In the above-described embodiment, the second pressing operation part 12 is operated by the user to start the supply of the second reagent 46, and to change the color of the color development region L3 to orange color, and then the cartridge 100 is loaded into the assay apparatus 110. For example, as the assay apparatus, there is also an apparatus in which the cartridge 100 in a state where the supply of only the first reagent 41 is started is loaded, and the second pressing operation part 12 is operated by an internal mechanism. In such an assay apparatus, since the cartridge 100 is loaded in a state where the color development region L3 is a dark green color before the color change, it is possible to acquire an observation image of the color development region L3 before the color change. By using the observation images before and after the color change, it is possible to detect the change in the color of the color development region L3. The position of the color development region L3 may be detected based on the change in the color of the color development region L3.

The observation image PG and the observation image PR described above are images obtained by trimming a part from the captured image imaged by the detection unit 114. An example of this trimming processing by the processor 120 is described below.

(Trimming Processing)

The processor 120 may execute the following trimming processing of trimming the observation image from the captured image imaged by the detection unit 114.

Figure 15:
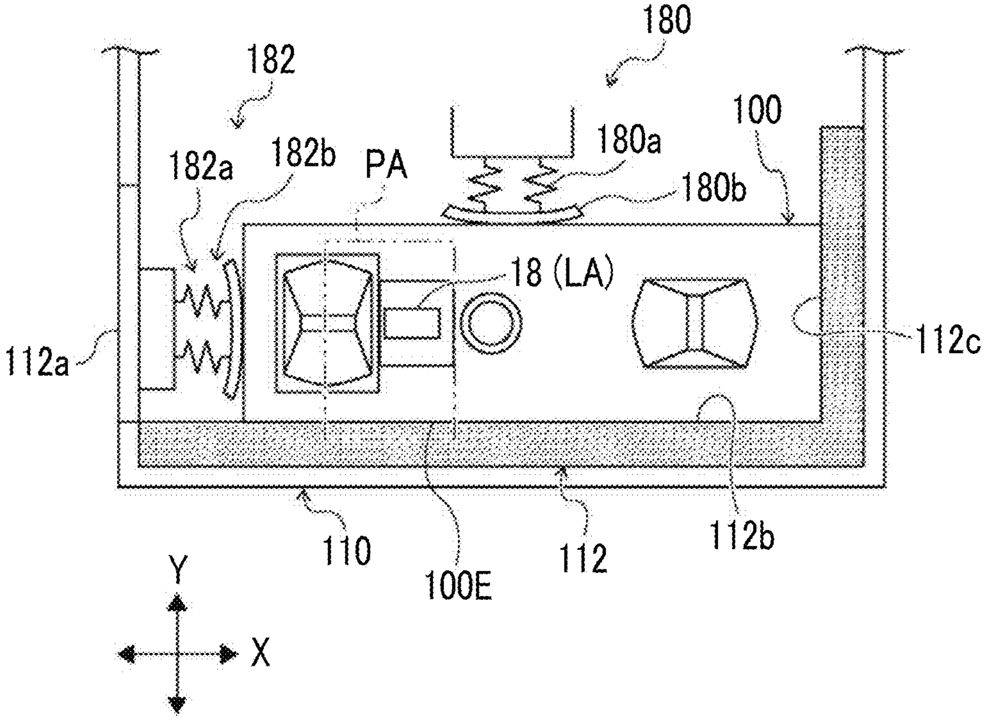
FIG. 15 is a plan view showing a cartridge in a state of being positioned by the biasing unit.

In order to execute this trimming processing, as shown in FIG. 15, biasing unit 180 and 182 for pressing the cartridge 100 against the reference surfaces 112*b* and 112*c* of the cartridge loading part 112 are provided inside the assay apparatus 110. The reference surfaces 112*b* and 112*c* are a surface along the insertion direction (X direction) of the cartridge 100 and a surface along a direction (Y direction) orthogonal to the surface in plane view, respectively.

The biasing unit 180 includes a spring 180*a* and a pressing body 180*b* to bias the cartridge 100 in the Y direction. The pressing body 180*b* is fixed to one end part of the spring 180*a*. The other end part of the spring 180*a* is fixed to the inside of the assay apparatus 110.

In addition, the biasing unit 182 includes a spring 182*a* and a pressing body 182*b* to bias the cartridge 100 in the X direction. The pressing body 182*b* is fixed to one end part of the spring 182*a*. The other end part of the spring 182*a* is fixed to the interior of the opening and closing lid 112*a* and biases the cartridge 100 in the X direction as the cartridge 100 is loaded into the assay apparatus 110.

Since the cartridge 100 has a rectangular shape, the end surface of the cartridge 100 is disposed along the reference surface 112*b* and 112*c* by being pressed against the reference surfaces 112*b* and 112*c* by the biasing unit 180 and 182, whereby the cartridge 100 is positioned.

Here, in FIG. 15, the captured image PA imaged by the detection unit 114 is shown by a two-dot chain line. The captured image PA includes at least a part of the outline of the cartridge 100. In the present embodiment, a part of the edge surface 100E is included. A part of the edge surface 100E corresponds to a part of the outline of the cartridge 100. The captured image PA includes the entire observation window 18.

Figure 16:
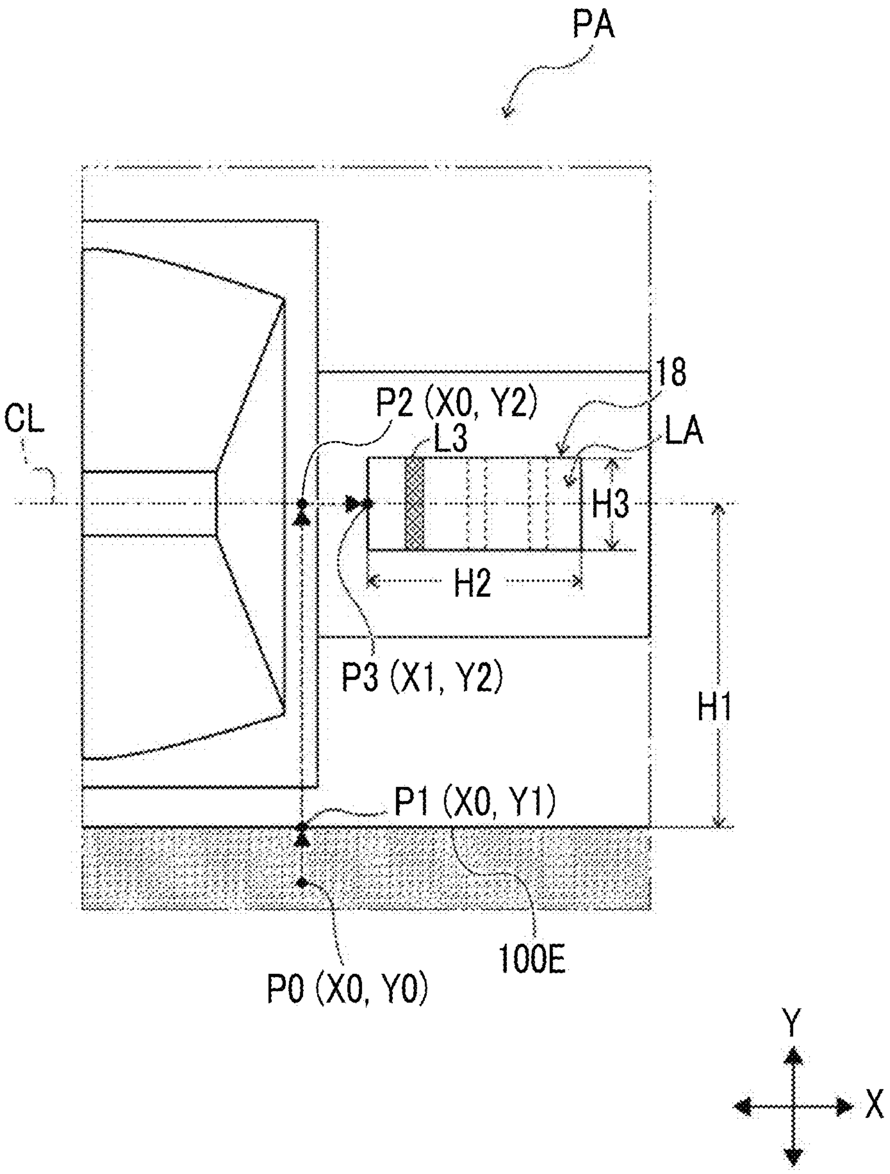
FIG. 16 is a diagram showing a captured image by the detection unit.

In FIG. 16, the outer edge of the captured image PA is drawn by a two-dot chain line. The processor 120 trims the observation region LA from the captured image PA. The observation region LA is a region interior the observation window 18. The trimming processing by the processor 120 is executed between Step S500 and Step S600 shown in FIG. 9. In addition, this trimming processing is executed by the assay region specifying unit 123 shown in FIG. 8.

As shown in FIG. 16, the processor 120 searches the edge surface 100E in the captured image PA. For example, In the captured image PA, the processor 120 searches the captured image PA in the Y direction from a predetermined point P0 (X0, Y0), and detects the position P1 (X0, Y1) of the edge surface 100E in the Y direction. In the captured image PA, the processor 120 detects a portion in which the contrast is not less than the threshold value as the edge surface 100E.

In order to facilitate this search, it is preferable that the cartridge 100 is formed of a white color resin and the cartridge loading part 112 is formed of a resin other than white color (for example, black). Alternatively, it is preferable that the cartridge 100 and the cartridge loading part 112 are formed of resins having high contrast in color therebetween.

Next, the processor 120 detects the position P2 (X0, Y2) offset from the position P1 in the Y direction by a distance H1 as the center position of the observation region LA to be trimmed, in the Y direction. This distance H1 is a distance from the edge surface 100E to the center line CL of the observation window 18.

In the cartridge 100, the distance H1 from the edge surface 100E to the center line CL of the observation window 18 is a unique value determined by the cartridge type. The distance H1 corresponding to the type of the cartridge 100 is stored in the memory 121 in advance.

Next, the processor 120 searches the end part of the observation window 18 in the X direction in the captured image PA. At this time, in the captured image PA, the processor 120 searches the inside of the captured image PA from the position P2 (X0, Y2) along the X direction, and detects the point P3 (X1, Y2), which is an end part of the observation window 18 in the X direction. Since the observation window 18 is an opening formed in the case 9 of the cartridge 100, the inner peripheral wall corresponding to the end part of the observation window 18 and the carrier 2 are not on the same plane, and the carrier 2 is recessed one step with respect to the inner peripheral wall. Therefore, the end part of the observation window 18 appears as a shadow in the captured image PA. The processor 120 detects an end part of the observation window 18 that appears as a shadow in the captured image PA as a point P3.

Next, the processor 120 trims a region having a width H2 in the X direction from the point P3 and having a width H3 in the Y direction with the line CL in the center as an observation region LA. The shape in which the width in the X direction is the width H2 and the width in the Y direction is the width H3 is the size of the observation window 18 in the cartridge 100, and these values are also stored in the memory 121 in advance. Here, the center of the width H3 is determined by the center line CL, but the center of the width H3 is not necessary to be the center line CL, and the region having the width H3 may be trimmed with the substantially center line CL (the vicinity of the center line CL) in the center. In this way, in the assay apparatus 110 of the present embodiment, by pressing the cartridge 100 against the reference surfaces 112*b* and 112*c*, the misregistration of the cartridge 100 in the cartridge loading part 112 is eliminated. Therefore, the position of the outline with the edge surface 100E in the captured image PA imaged is likely to be uniquely determined as compared with the case where the misregistration of the cartridge 100 occurs. Therefore, the search of the outline is simplified.

Furthermore, since the distance H1 from the outline to the center line CL of the observation window 18 can be grasped in advance, the observation region LA can be easily specified by searching the observation window 18 with reference to the outline.

In addition, by executing the trimming processing of the observation region LA, the search range of the color development region L3 as the index region is narrowed as compared with a case where the trimming processing is not executed, and thus the detection of the color development region L3 can be performed easily and quickly.

Figure 17:
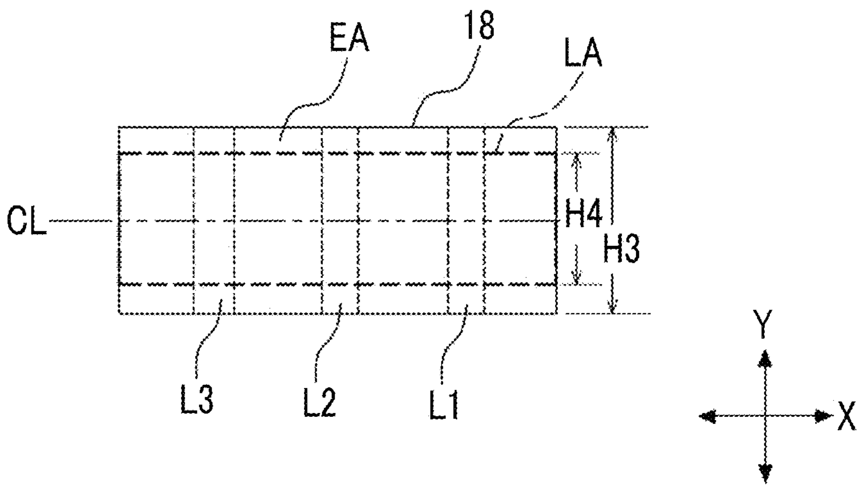
FIG. 17 is a diagram showing an observation region of another example.

In the above example, the processor 120 searches the observation window 18 with reference to the edge surface 100E forming the outline of the cartridge 100, and executes the region-specifying processing for specifying a region substantially corresponding to the size of the observation window 18, that is, an exposed region EA exposed to the observation window 18 as the observation region LA. On the other hand, as shown in FIG. 17, the processor 120 may execute the region-specifying processing for specifying a region in which the width in the Y direction is narrower than that of the exposed region EA exposed to the observation window 18 as the observation region LA. In the example shown in FIG. 17, a region having a width H4 (here, H4<H3) in the Y direction with the center line CL in the center is specified as the observation region LA with respect to the width H3 in the Y direction of the observation window 18.

Figure 18:
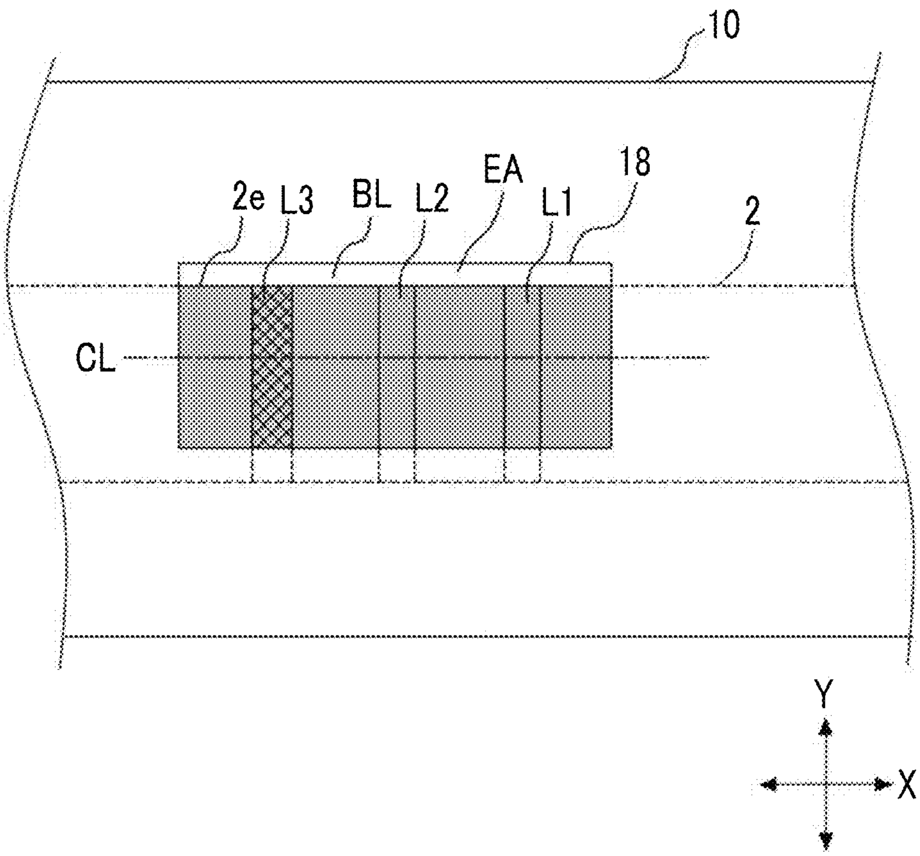
FIG. 18 is a diagram showing an example in which an end part of the carrier is exposed to an exposed region observed from an observation window.
Figure 19:
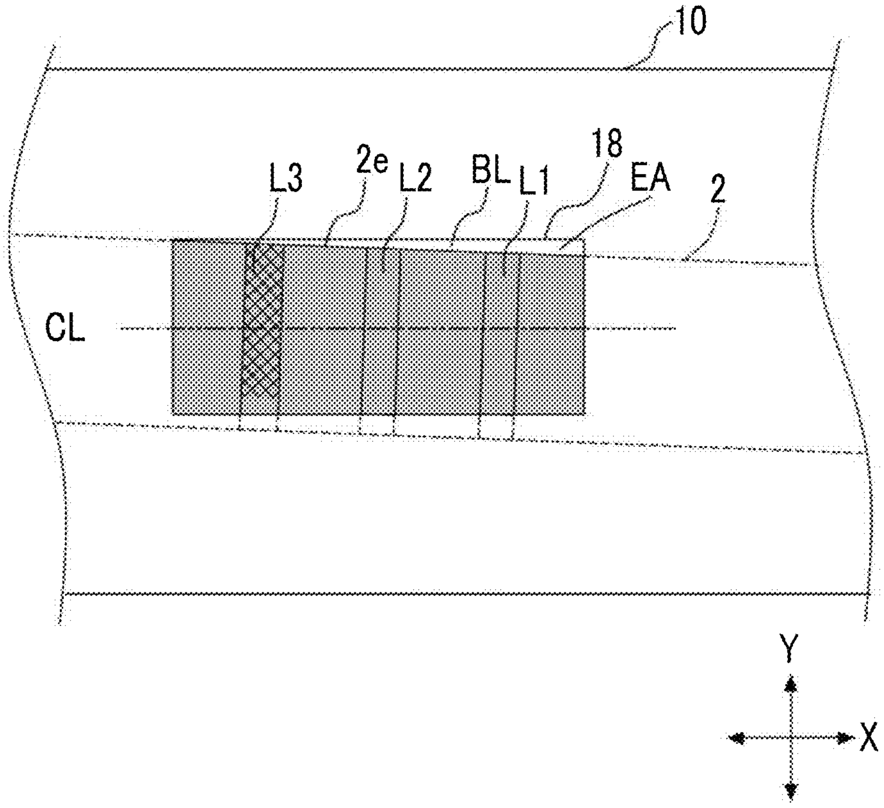
FIG. 19 is a diagram showing another example in which the end part of the carrier is exposed to an exposed region observed from an observation window.

For example, in a case where the case main body 20 and the carrier 2 are disposed to be displaced from each other when the carrier 2 is assembled to the case main body 20, the end part 2*e* of the carrier 2 in the width direction may be exposed in the exposed region EA exposed to an observation window 18 provided in the cover member 10. In a case where the case main body 20 and the carrier 2 are disposed to be displaced from each other in the width direction (Y direction) of the case main body 20, as shown in FIG. 18, the end part 2*e* of the carrier 2 in the width direction may be exposed to the upper end region of the exposed region EA. In addition, depending on the direction of the displacement, the end part 2*e* of the carrier 2 in the width direction may be exposed to the lower end region of the exposed region EA. Furthermore, in a case where the longitudinal direction of the carrier 2 is inclined with respect to the longitudinal direction of the case main body 20, as shown in FIG. 19, the end part 2*e* of the carrier 2 in the width direction may be exposed to apart of the upper end region or a part of the lower end region of the exposed region EA. As shown in FIG. 18 and FIG. 19, the specification of the exposed region EA as the observation region LA in a case where a blank region BL in which the carrier 2 is absent is generated in the exposed region EA, is obstruction when the color development state of the assay region L1 is detected and the determination of whether the sample is positive or negative is performed. In FIG. 18 and FIG. 19, the carrier 2 in the exposed region EA is shown in gray color in order to facilitate the visual recognition of the carrier 2 and the blank region BL in which the carrier 2 is absent. The same applies to FIG. 20 described later.

As shown in FIG. 17, in a case where a region in which the width in the Y direction is narrower than that of the exposed region EA is specified as the observation region LA, a blank region BL generated in a case where the case main body 20 and the carrier 2 are disposed in the observation region LA to be displaced from each other can be provided not to be included, and thus the determination of the assay region L1 can be performed with high accuracy.

As an example, the width H4 is a predetermined value as a range that does not include the blank region BL expected to generate in a case where the case main body 20 and the carrier 2 are disposed to be displaced from each other, and may be stored in the memory 121 in advance. In this case, the processor 120 detects a point P3 (X1, Y2) which is a point on the frame line of the observation window 18 and is an end part of the observation window 18 in the X direction, and then executes the region-specifying processing for specifying a region having a width H2 in the X direction from the point P3 and having a width H4 in the Y direction with the center line CL as the center line, as the observation region LA.

As described above, in a case of specifying the observation region LA in which the width in the Y direction is narrower than that of the exposed region EA, the processor 120 can specify the observation region LA using the preset width H4. In addition, the processor 120 may specify the observation region by searching a boundary between the frame line of the observation window 18 and the carrier 2 or a boundary between the blank region BL in a region (here, exposed region EA) within the frame line and the carrier 2. For example, the processor 120 can specify the observation region LA as follows.

Figure 20:
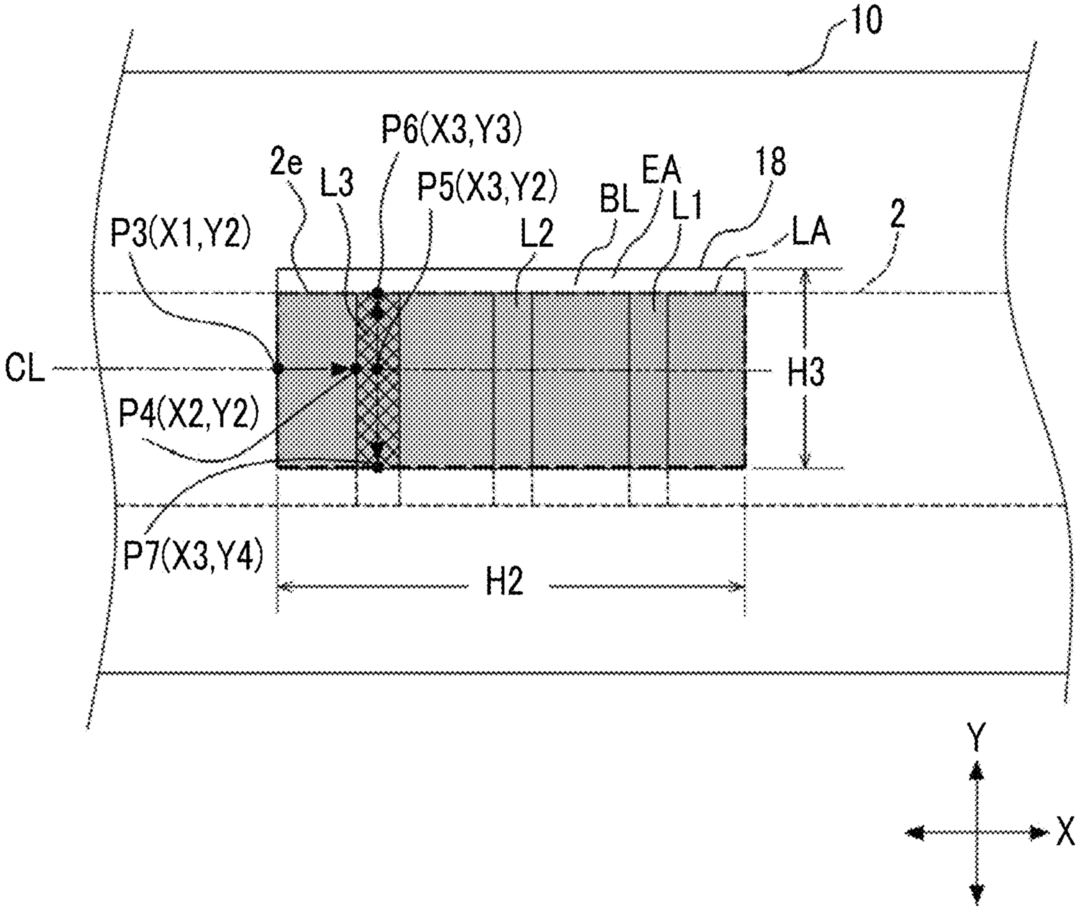
FIG. 20 is an explanatory diagram of a region-specifying processing for specifying the observation region.

The processor 120 executes the same processing as the search method described above until detecting the point P3 (X1, Y2), which is an end part of the observation window 18 in the X direction. The point P3 (X1, Y2) corresponds to at least a part of the observation window 18. After that, as shown in FIG. 20, the processor 120 specifies a frame line surrounding a region having the width H2 in the X direction from the point P3 (X1, Y2) and having the width H3 in the Y direction with the center line CL in the center, as the frame line of the observation window 18. The interior of the frame line is the exposed region EA exposed from the observation window 18. The processor 120 searches a portion where the density changes significantly in the X direction from the point P3 (X1, Y2), and thus detects the point P4 (X2, Y2) on one end in the X direction of the color development region L3 as an index region in the exposed region EA. Then, the processor 120 specifies the point P5 (X3, Y2) in the color development region L3 with reference to the point P4 (X2, Y2). The width of the color development region L3 in the X direction is known as the coating width of the color development region L3. Since the point P4 (X2, Y2) is the downstream side end of the color development region L3, any point P5 (X3, Y2) within the width of the color development region L3 is specified from X2.

After that, the processor 120 searches a portion where the density changes significantly in the Y direction from the point P5 (X3, Y2), and thus searches a boundary between the carrier 2 and the frame line or a boundary between the carrier 2 and the blank region BL in a region within the frame line. In the present example, the processor 120 searches a portion where the density changes significantly in the Y direction from the point P5 (X3, Y2). By this search, the processor 120 detects the point P6 (X3, Y3) of one end (upper end in the figure) of the color development region L3 in the Y direction in the exposed region EA and the point P7 (X3, Y4) of the other end (lower end in the figure) of the color development region L3 in the Y direction. Here, the point P6 (X3, Y3) is a point on the boundary between the carrier 2 and the blank region BL in the region within the frame line, and the point P7 (X3, Y4) is a point on the boundary between the carrier 2 and the frame line.

Then, the processor 120 specifies, from the exposed region EA, a region within a range from Y3 to Y4 in the Y direction as the observation region LA.

In a case of specifying the observation region LA in which the width in the Y direction is narrower than that of the exposed region EA, in the Y direction of the exposed region EA, the processor 120 preferably specifies a region where the color development region L3 is present, that is, a region where the carrier 2 is present, as the observation region LA. Even in a case where the case main body 20 and the carrier 2 are displaced more than expected and the blank region BL is present more than expected, the blank region BL can be excluded by searching the region where the carrier 2 is present and specifying the observation region LA, and a decrease in assay accuracy can be suppressed. In addition, in a case where a region having a preset width H4 is specified as the observation region LA, a region other than the blank region BL may be largely excluded, but by searching a region where the carrier 2 is present to specify the observation region LA, the region of the effective carrier 2 can be used without being excluded.

The above-described embodiment describes the form in which the observation region LA is irradiated with the illumination light from the light source 115, and the reflected light reflected by the observation region LA is received by the detection unit 114, but may be the form in which instead of the reflected light, the transmitted light having transmitted through the observation region LA is received by the detection unit 114. In this case, for example, the detection unit 114 and the light source 115 are disposed at positions facing each other with the carrier 2 on which the observation region LA is formed interposed therebetween. That is, in a case where the surface of the carrier 2 on which the observation region LA is formed is set as the front surface, the detection unit 114 is disposed at a position facing the front surface, and the light source 115 is disposed at a position facing the back surface. Accordingly, the illumination light emitted by the light source 115 is incident on the back surface of the carrier 2, and the transmitted light having transmitted through the observation region LA from the back surface toward the front surface can be received by the detection unit 114. Since the transmitted light includes the information of the observation region LA, the detection unit 114 can acquire the captured image PA by receiving the transmitted light. The technology of the present disclosure may be applied to the assay apparatus in such a form that the transmitted light of the observation region LA is received.

In addition, in the above-described embodiment, the assay apparatus 110 is described as an example of an apparatus used for assaying a sample of a subject in a medical facility such as a hospital, but in the process of developing the cartridge 100, the assay apparatus 110 may be used to evaluate the performance of the cartridge 100 by the maker manufacturing the cartridge 100.

In the above-described embodiment, as the processor 120 and a hardware structure of a processing unit as internal configurations of the processor 120, which executes various types of processing, such as a detection unit control unit 122, an assay region specifying unit 123, a color development state discrimination unit 124, and a display control unit 125, various processors shown below can be used. The various processors include, for example, a CPU which is a general-purpose processor executing software to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of these various processors, or may be configured by a combination of two or more processors having the same type or different types (for example, a combination of a plurality of FPGAs and/or a combination of a CPU and an FPGA). In addition, a plurality of processing units may be configured with one processor.

As an example in which a plurality of processing units are configured into a single processor, there is a form in which a single processor is configured by a combination of one or more CPUs and software, and this processor functions as a plurality of processing units. A second example of the configuration is an aspect in which a processor that implements the functions of the entire system including a plurality of processing units using one integrated circuit (IC) chip is used. A representative example of this aspect is a system on chip (SoC). In this way, various processing units are configured by one or more of the above-described various processors as hardware structures.

Furthermore, specifically, an electric circuit (circuitry) obtained by combining circuit elements, such as semiconductor elements, can be used as the hardware structure of the various processors.

The present disclosure is not limited to the above embodiments, and can be implemented with appropriate modifications, such as omitting a configuration or replacing a configuration with a different configuration within the scope that does not deviate from the gist of the present disclosure.

What is claimed is:

1. An assay apparatus used for immunochromatographic assay, the assay apparatus comprising:
- a loading part into which a cartridge including a carrier and a case configured to accommodate the carrier is attachably and detachably to be loaded, the carrier having an assay region in which a color development state changes depending on whether a sample is positive or negative, and an index region which is disposed with a predetermined interval from the assay region and which is optically distinguishable from the assay region regardless of whether the sample is positive or negative;
- a light source configured to illuminate an observation region on the carrier including the assay region and the index region;
- an imaging unit configured to image the observation region; and
- a processor configured to acquire an image including the observation region from the imaging unit, configured to detect a position of the index region from the image, and configured to specify a position of the assay region with reference to the position of the index region;
- further configured to execute a trimming processing in which the observation region is cut out from the image, and which includes a region-specifying processing in which the observation region is specified, in the image, by searching an outline of the cartridge and by searching at least a part of an observation window with reference to the searched outline of the cartridge; and
- wherein the region-specifying processing in the trimming processing is a processing in which the observation region is configured to be specified by searching the at least a part of the observation window of the cartridge in the image to specify a frame line of the observation window, and further by being configured to search a boundary between the frame line and the carrier or a boundary between a blank in a region within the frame line and the carrier.

2. The assay apparatus according to claim 1,
wherein the index region is a region in which a color development state changes by reacting with a reagent.

3. The assay apparatus according to claim 1,
wherein the processor is configured to detect the position of the index region based on an optical density of the index region.

4. The assay apparatus according to claim 3,
wherein as the optical density, in the carrier, a ΔOD value, which is a difference between an optical density in the index region and an optical density in a background region serving as a background of the index region, is used.

5. The assay apparatus according to claim 1,
wherein the processor is configured to detect the position of the index region based on a form of the index region.

6. The assay apparatus according to claim 1,
wherein the light source is a white color light source,
the image is a color image, and the processor is configured to detect the position of the index region based on a color of the index region.

7. The assay apparatus according to claim 2, wherein in a case where the index region is a first color before reacting with the reagent and changes from the first color to a second color by reacting with the reagent, the light source includes a first monochromatic light source that emits first monochromatic light in which an amount of reflected light is larger in a case where the index region of the first color is irradiated as compared with a case where the index region of the second color is irradiated, and a second monochromatic light source that emits second monochromatic light in which an amount of reflected light is larger in a case where the index region of the second color is irradiated as compared with in a case where the index region of the first color is irradiated, and the processor is configured to acquire a first image obtained by imaging the index region of the second color using the first monochromatic light source and the imaging unit, acquire a second image obtained by imaging the index region of the second color using the second monochromatic light source and the imaging unit, and detect the position of the index region based on the first image and the second image.

8. The assay apparatus according to claim 7, wherein the first color includes a green color component, the second color is orange color, the first monochromatic light source is a green color light source, and the second monochromatic light source is a red color light source.

9. The assay apparatus according to claim 2, wherein the reagent is an amplifying liquid for amplifying the change in the color development state of the assay region, and the color development state of the index region changes by reacting with the amplifying liquid.

10. The assay apparatus according to claim 1, wherein the index region is a region in which a color development state changes by reacting with a labeling substance.

11. The assay apparatus according to claim 1, wherein in the cartridge, the assay region and the index region are regions formed by coating on the carrier, and the carrier is assembled to the case after the assay region and the index region are formed.

12. The assay apparatus according to claim 1, wherein the observation window configured to observe the observation region from an outside is formed in the cartridge, both of an outer shape of the cartridge and the observation window have a rectangular shape, the assay apparatus further includes a biasing unit configured to pressing an edge surface of the cartridge attached to the loading part against a reference surface, and the processor is configured to acquire, from the imaging unit, the image obtained by being configured to image a region at least including the observation window and a part of the outline of the cartridge in a state where the cartridge is configured to be pressed against the reference surface.

* * * * *